US008353845B2

(12) United States Patent
McCawley et al.

(10) Patent No.: US 8,353,845 B2
(45) Date of Patent: *Jan. 15, 2013

(54) APPARATUS AND METHOD FOR DELIVERY OF AN AEROSOL

(75) Inventors: Michael McCawley, Morgantown, WV (US); Gary Gasner, Morgantown, WV (US); Ian Christie, Morgantown, WV (US); Tal Gottesman, Morgantown, WV (US); James Dalton, Morgantown, WV (US)

(73) Assignee: Respiratory Management Technology, Morgantown, WV (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/162,017

(22) Filed: Jun. 16, 2011

(65) Prior Publication Data

US 2011/0247611 A1    Oct. 13, 2011

Related U.S. Application Data

(62) Division of application No. 12/771,151, filed on Apr. 30, 2010, now Pat. No. 7,988,641, which is a division of application No. 11/771,479, filed on Jun. 29, 2007, now Pat. No. 7,731,666, which is a division of application No. 10/652,561, filed on Sep. 2, 2003, now Pat. No. 7,241,269.

(51) Int. Cl.
*A61B 5/08* (2006.01)

(52) U.S. Cl. .... 600/538; 600/300; 600/529; 128/200.24

(58) Field of Classification Search .......... 600/529–543; 129/200.24–207.18; 128/200.24–207.18
See application file for complete search history.

(56) References Cited

U.S. PATENT DOCUMENTS

| | | | |
|---|---|---|---|
| 4,067,320 A | 1/1978 | Olsson et al. | |
| 4,307,730 A | 12/1981 | Korn | |
| 4,370,986 A | 2/1983 | Gebhart et al. | |
| 4,517,987 A | 5/1985 | Sackner et al. | |
| 5,058,600 A | 10/1991 | Schechter et al. | |
| 5,224,487 A * | 7/1993 | Bellofatto et al. | 600/538 |
| 5,906,202 A * | 5/1999 | Schuster et al. | 128/203.23 |
| 6,068,602 A | 5/2000 | Tham et al. | |
| 6,135,105 A | 10/2000 | Lampotang et al. | |
| 6,302,851 B1 | 10/2001 | Gedeon | |
| 6,390,092 B1 | 5/2002 | Leenhoven | |
| 6,544,191 B2 | 4/2003 | Koch et al. | |
| 6,585,662 B1 | 7/2003 | Jones et al. | |
| 7,731,666 B2 * | 6/2010 | McCawley et al. | 600/532 |

* cited by examiner

*Primary Examiner* — Navin Natnithithadha
*Assistant Examiner* — Karen Toth
(74) *Attorney, Agent, or Firm* — Connolly Bove Lodge & Hutz LLP

(57) ABSTRACT

An apparatus for measuring lung ventilation, comprising: a pressure device to measure volume of air flow; an aerosol-generating device that provides aerosol particles to be released at a determined point in a breathing cycle; a mouthpiece with a detector that measures the concentration of aerosol particles for a given volume during the breathing cycle; and a computing device configured to provide lung ventilation data as a function of time constants.

7 Claims, 11 Drawing Sheets

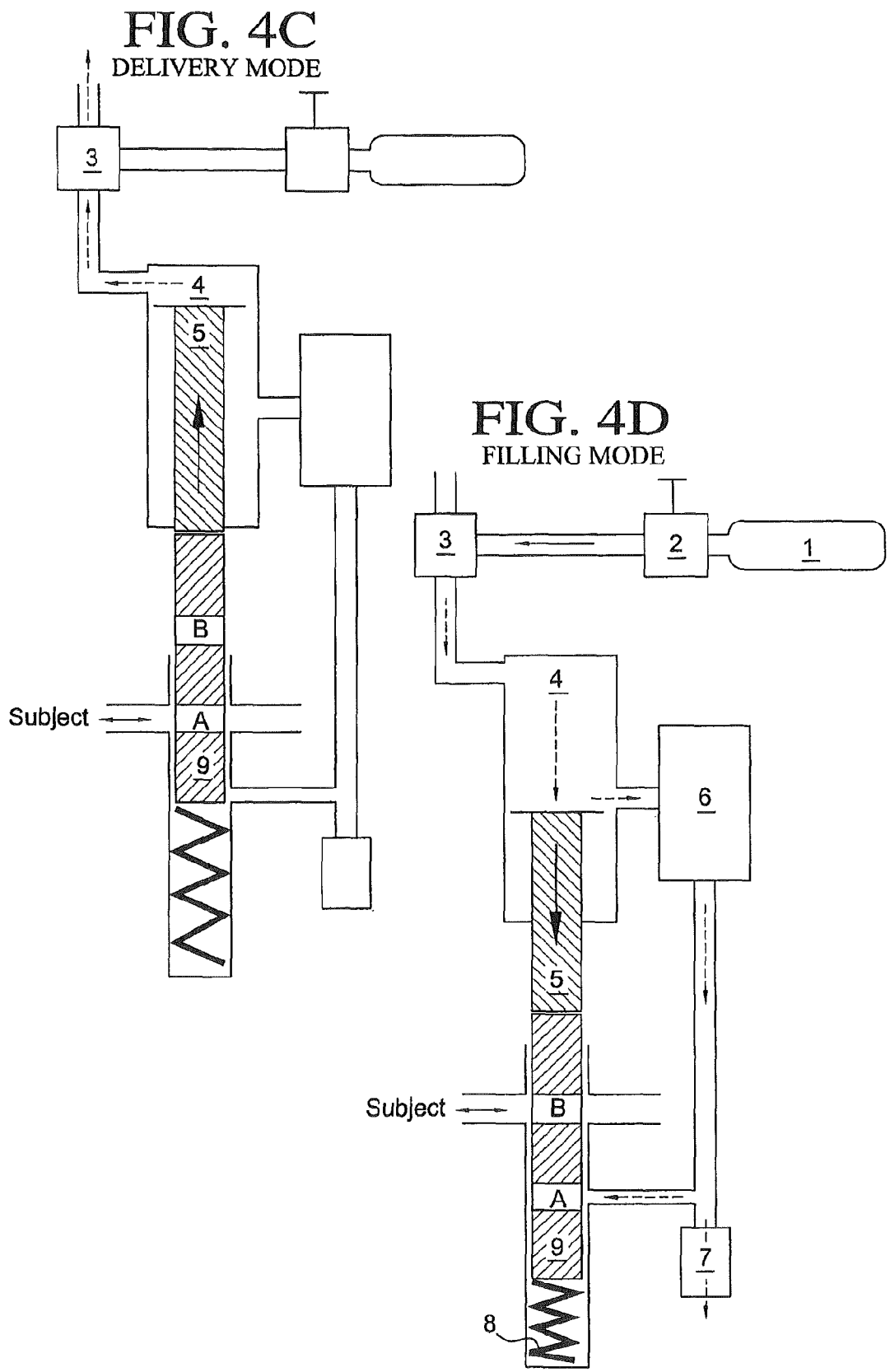

```
501 ─ CONTROL VOLUME OF DRIFT
         │
502 ─ MEASURE PRESSURE DATA DURING INHALATION/EXHALATION
         │
503 ─ CALCULATE VOLUME OF INHALATION/EXHALATION FROM PRESSURE DATA
         │
504 ─ ANALYZE VOLUME OF INHALATION & DETERMINE VOLUME OF PENETRATION ($V_p$)
         │
505 ─ INJECT AREOSOL BOLUS AT A SELECTED TIME DURING INHALATION → $V_p$
         │
506 ─ MEASURE LIGHT DATA DURING INHALATION/EXHALATION
         │
507 ─ ANALYZE LIGHT DATA TO DETERMINE PARTICLE CONCENTRATION (INHALATION)
         │
508 ─ PREDICT LUNG VENTILATION BY CALCULATING PARTICLE (EXHALATION) CONCENTRATION FROM PARTICLE CONCENTRATION (INHALATION)
         │
509 ─ DISPLAY PREDICTED LUNG VENTILATION
```

FIG. 5

```
601 — CONTROL VOLUME OF DRIFT
  ↓
602 — MEASURE PRESSURE DATA DURING INHALATION/EXHALATION
  ↓
603 — CALCULATE VOLUME OF INHALATION/EXHALATION FROM PRESSURE DATA
  ↓
604 — ANALYZE VOLUME OF INHALATION & DETERMINE VOLUME OF PENETRATION ($V_p$)
  ↓
605 — INJECT AREOSOL BOLUS AT A SELECTED TIME DURING INHALATION → $V_p$
  ↓
606 — MEASURE LIGHT DATA DURING INHALATION/EXHALATION
  ↓
607 — ANALYZE LIGHT DATA TO DETERMINE PARTICLE CONCENTRATION (INHALATION) TIME CONSTANTS (EXHALATION)
  ↓
608 — PREDICT LUNG VENTILATION BY CALCULATING PARTICLE (EXHALATION) CONCENTRATION FROM PARTICLE CONCENTRATION (INHALATION)
  ↓
609 — DISPLAY PREDICTED LUNG VENTILATION
  ↓
610 — MEASURE LUNG VENTILATION BY COMPARING EXHALATION PARTICLE CONCENTRATION WITH TIME CONSTANT DISTRIBUTION (MEASURED)
  ↓
611 — DISPLAY MEASURED TIME CONSTANTS
```

FIG. 6

APPARATUS AND METHOD FOR DELIVERY OF AN AEROSOL

CROSS-REFERENCE TO RELATED APPLICATIONS

Priority is claimed as a divisional application to U.S. patent application Ser. No. 12/771,151, filed Apr. 30, 2010, which claims priority as a divisional application to U.S. Pat. No. 7,731,666, issued Jun. 8, 2010, which claims priority as a divisional application to U.S. Pat. No. 7,241,269, issued Jul. 10, 2007. The disclosures of the aforementioned priority documents are incorporated herein by reference in their entirety.

FIELD OF THE INVENTION

This invention relates to an apparatus and method for the delivery of an aerosol. The apparatus and method is used to identify an aerosol inhalation volume at which lung dysfunction occurs, by measuring lung ventilation at specific volumes of inhalation.

BACKGROUND OF THE INVENTION

The lungs may be characterized as a mass exchanger in which oxygen is delivered through the alveoli to blood and carbon dioxide is removed from the blood for exhalation. The efficiency of the lungs, in terms of the exchange of gaseous materials at the blood/gas interface, is dependent in-part on the ventilation of each lung. The term "ventilation" refers to the movement of or the exchange of oxygen-rich air from outside the body into the lung where the air is mixed with relatively oxygen deficient air through the course of breathing. The ventilation function of a patient's lungs can be determined and monitored by measuring the resistance and compliance of the airways of the lung.

The resistance and compliance within different regions of the lungs affect the distribution of pulmonary ventilation. The term "resistance" refers to the flow resistance due to an obstruction or a restriction within a respiratory passageway to the passage or flow of a gas to and from the lungs. The measured unit of resistance is $H_2O$/(liters/see). The term "compliance" refers to the flexibility or elasticity of the lungs as they expand and contract during a respiratory cycle. The measured unit of compliance is liters/(cm-$H_2O$). If one multiplies resistance and compliance, the unit of time (e.g., seconds) that remains is referred to as a "time constant." Therefore, the ventilation function of a patient's lungs can be represented by a single value, that is, the time constant.

Spirometry is one technique used to diagnose and monitor respiratory disease. In spirometry, the patient inhales as deeply as possible, and then exhales until all air is completely expelled from the lungs. As one can imagine, this requires a great deal of concentration and effort by the patient, and thus, spirometry readings largely depend on how well the patient is feeling and breathing on a given day. Spirometry measures only the flow volume of air that is inhaled and/or exhaled by the patient. Spirometry does not measure resistance or compliance, and does not rely on the calculation of time constants to determine lung function or lung ventilation. Also, spirometry is relatively insensitive for measurements of small airways and thus has limited use for diagnosis of respiratory diseases in these areas of the lung such as asthma and emphysema. Consequently, spirometry is a relatively insensitive technique for monitoring and diagnosing the most prevalent of respiratory diseases.

U.S. Pat. No. 6,135,105 by Lampotang et al. describes a method of classifying each lung by measuring variations in pressure or flow rates using an invasive endotrachael tube equipped with a pressure sensor. Time constants are computed as the product of measured resistance and compliance. However, it is known that this procedure does not accurately account for convective transport in the small airways of the lung, and thus, can result in significant errors in measurement. Consequently, the accuracy of the resistance and compliance values, and thus, the calculated time constants measured using this procedure are questionable. Also, one cannot ignore the need for the endotrachael tube and the resulting discomfort of the patient due to this invasive procedure.

As a result, there is a need for an apparatus and method for correctly diagnosing and accurately monitoring respiratory disease in a patient without relying on the patient's ability to breath on a particular day or without having to insert an invasive device (e.g., endotrachael tube) into the patient.

SUMMARY OF THE INVENTION

One aspect of the present invention is directed to an apparatus for measuring lung ventilation, comprising a pressure device to measure volume of air flow; an aerosol-generating device that provides aerosol particles to be released at a determined point in a breathing cycle; a mouthpiece with a detector that measures the concentration of aerosol particles for a given volume during the breathing cycle; a computing device configured to provide lung ventilation data as a function of time constants; and a multi-port coupling device configured to couple the computing device, mouthpiece, aerosol-generating device and pressure device.

Another aspect of the present invention is directed to a method for measuring lung ventilation. The method comprises: measuring pressure data and calculating volumes of airflow of a plurality of respiratory cycles, providing a volume of penetration, providing an aerosol bolus at a determined point of the breathing cycle, measuring concentration values of aerosol particles, and calculating time constants from the volume of penetration and the measured aerosol concentration values.

Yet another aspect of the present invention is directed to determining the position of an obstruction in the upper region of the lungs associated with specific volumes of air inhaled into the lung which, in turn, are associated with air traveling through certain branches in the lung which may be restricted or obstructed due to disease or injury. The method comprises: a.) measuring pressure data and calculating volume of airflow of a breathing cycle; b.) providing a volume of penetration; c.) providing an aerosol bolus at a determined point of the breathing cycle; d.) measuring a concentration values of aerosol particles and calculating time constants from the volume of penetration and the measured aerosol concentration values; f.) repeating steps b to d using a different volume of penetration; and g.) comparing the calculated time constants from at least two provided volumes of penetration.

Yet again, another aspect of the present invention is a method for determining aerosol particle concentrations, comprising: measuring inhaled and exhaled aerosol concentrations at discrete values of at least one of time, volume and dimensionless volume; estimating initial values for intrinsic mixing on inhalation, intrinsic mixing on exhalation, effective volume of lung on inhalation, and effective volume of lung on exhalation; minimizing the estimated initial values; determining a volume of penetration; estimating inhaled aerosol concentration as a function of the measured inhaled aerosol concentration and at least one of K(V) and K(t); and estimating exhaled particle concentration as a function of the estimated inhaled aerosol concentration and a probability that a particle exits the lung in a provided volume.

Another aspect of the invention comprises measuring breath holding time and the effect of that breath holding time on the particle concentration that is exhaled, the particle concentration being described as a percentage of the inhaled particle concentration as a function of the volume of penetration of the aerosol.

Yet, another aspect of the invention comprises determining a total amount or a percentage of a total amount of inhaled particulate material that is exhaled in the time of a given breath or in subsequent breaths after the breath in which an aerosol is inhaled. In addition, another, another aspect of the invention comprises recognizing materials that are used to generate an aerosol.

Further, another aspect of the invention comprises determining the retention of aerosol inhaled in a single breath and exhaled over the course of subsequent breaths as a diagnostic indicator of asthma.

Furthermore another aspect of the invention comprises means for determining a total amount or a percentage of a total amount of inhaled particulate material that is exhaled in the time of a given breath or in subsequent breaths after the breath in which an aerosol is inhaled. Moreover, another aspect of the invention comprises means for recognizing materials that are used to generate an aerosol.

BRIEF DESCRIPTIONS OF DRAWINGS

The invention will be better understood by reference to the Detailed Description of the Invention when taken together with the accompanying drawings, wherein:

FIG. 4c shows an exemplary 3-way valve in the "Filling Mode";

FIG. 4d shows an exemplary 3-way valve in the "Delivery Mode";

FIG. 5 shows an exemplary flow diagram for a method for predicting lung ventilation;

FIG. 6 shows an exemplary flow diagram for a method for measuring lung ventilation;

DETAILED DESCRIPTION OF THE PREFERRED EMBODIMENTS

Figure 1:
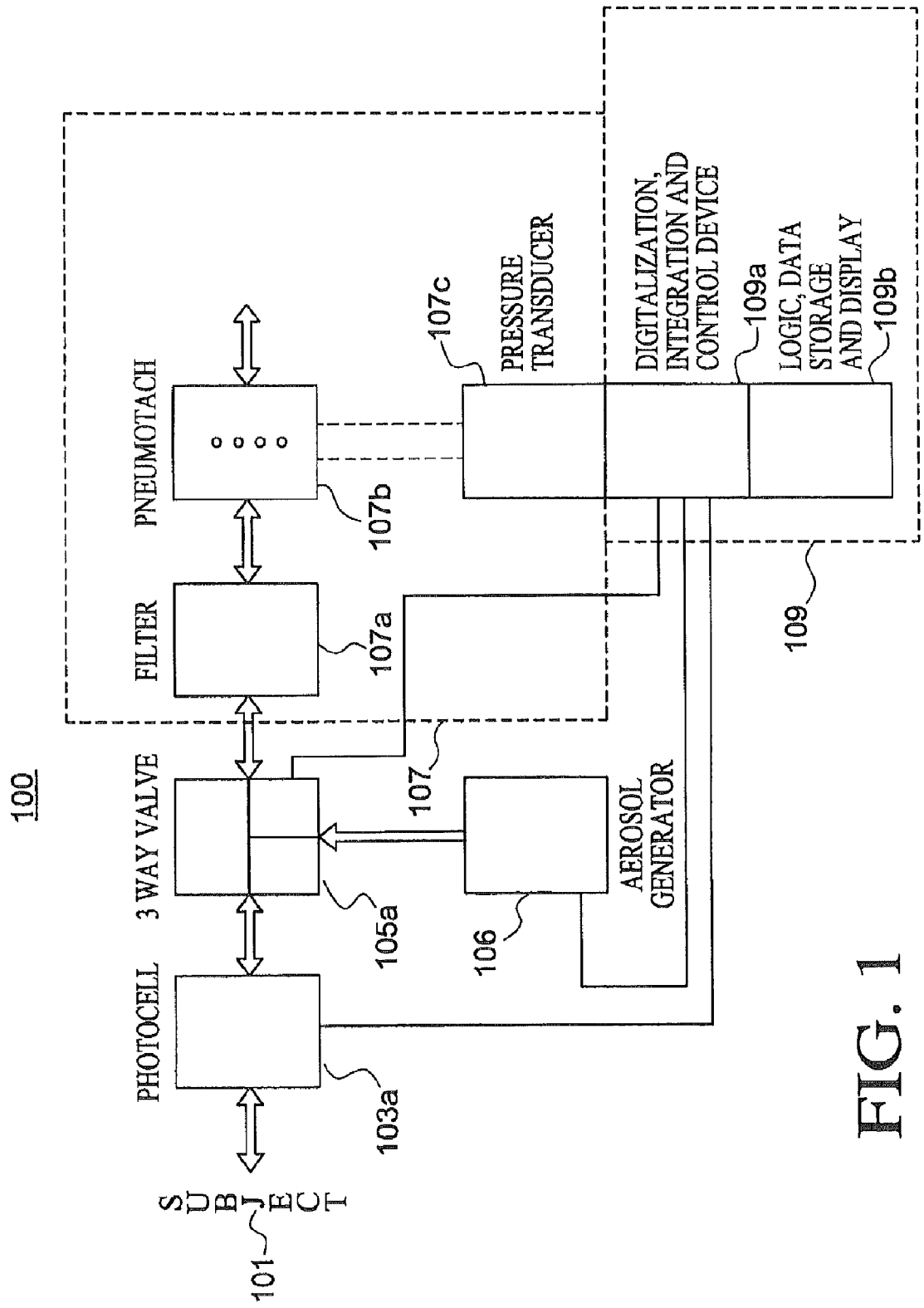
FIG. 1 depicts an exemplary embodiment of the invention.

The invention is directed to an apparatus for delivering an aerosol into the lungs of a patient. The apparatus measures lung ventilation associated with specific volumes of air inhaled into the lung which delivering an aerosol into the lungs of a patient. The inhaled air passes through certain branches in the lung, some of which may be restricted or obstructed due to disease or injury. The apparatus includes a pressure device, a detector, an aerosol-generating device, a multi-port coupling device and a computing device. The aerosol-generating device provides a bolus of aerosol particles to be released at a determined point in a breathing cycle. The computing device provides information on lung ventilation as a function of time constants. The aerosol particles are used to measure the time constants as the aerosol particles move in and out of the lung over a plurality of respiratory cycles. The term "breathing cycle" is defined as the time the patient begins to breathe through a mouthpiece of the invention to the time the patient completes the test. A "respiratory cycle" is defined as one inhalation-exhalation cycle. As a result, a breathing cycle includes a plurality of respiratory cycles for a patient.

The apparatus and method of the invention provides the physician as well as the patient with the ability to effectively monitor or treat chronic respiratory diseases irrespective of the health of the patient or how well the patient is able to breath on a given day. Unlike spirometry, a common technique used to diagnose and monitor respiratory disease in patients, the patient is not required to inhale and exhale deeply to obtain ventilation test data. Instead, the patient simply breathes into a mouthpiece of the apparatus using normal respiratory cycles. Also, the method of the invention can be performed by the patient, and without the need for a trained technician.

One significant advantage provided by the apparatus and methods of the invention is that the position of an obstruction or restriction in the upper regions of the lungs (e.g., the bronchial branches) can be identified and monitored. The apparatus and methods of the invention provide detailed information on the point(s) of obstruction or inflammation for a patient. The physician can monitor the progress of these point(s) of obstruction, and even determine if secondary points of obstruction develop. As a result, the apparatus and methods of the invention provide the physician with specific information on the respiratory condition for a patient.

Another significant advantage provided by the apparatus and methods of the invention is the localized delivery of an aerosol bolus containing an active pharmaceutical (e.g., a bronchial dilating agent) to the point of obstruction or inflammation. Once the point(s) of obstruction are identified in a particular patient by the invention, the active pharmaceutical is released into the air flow at the optimal point in a respiratory cycle. In this manner, the aerosolized agent is concentrated in a selected volume of air flow that will contact the point of obstruction.

The measurement of time constants can be an important diagnostic tool. A relatively large time constant suggests the presence of an obstruction or restriction in the lung and indicates some form of respiratory disease or impairment of lung function. As used in the medical sense, the term "obstruction" refers to impairment such as that found in bronchitis or emphysema whereas the term "restriction" refers to impairment such as that found in asthma. The existence of nearly equivalent time constants for each of the pathways to the small airways of the lung is referred to as "homogeneous ventilation" and is well recognized as a characteristic of healthy individuals. In contrast, unbalanced and longer time constants can be indicative of obstructions and restrictions and is referred to as "non-homogeneous ventilation."

Observed differences in regional time constants is suggestive of regional differences in convective ventilation rates.

Also, information on the severity of the obstruction(s) can be obtained from the time constant data. For example, patients with airway obstructions may have a relatively slow emptying of aerosol particles from bronchi compared to healthy patients. The more time it takes for the aerosol particles to leave the lung can be an indication of the severity of the diseased regions of the lung.

The apparatus and method of the invention provide an accurate and direct measurement of time constants relating to the small airways. This information is not available from spirometry, and allow the physician to more accurately diagnose and monitor respiratory diseases or impairments to lung function.

The apparatus of the invention measures the concentration of aerosol particles from an aerosol bolus with respect to time or volume during a breathing cycle. For any given flow measuring time or measuring volume can be considered an equivalent measurement of the penetration of particles into the lung. The aerosol particles move with the air that is inhaled and exhaled from the lung and the apparatus records the concentration and transit time or volume required for the particles to move into the lung and back out. In essence, the aerosol particles function as microscopic markers, which by measuring their concentration with respect to time or volume provide the necessary ventilation data for a patient. The release of a "pulse" or "bolus" of aerosol particles at some determined time during the breathing cycle, particularly the inhalation step, is one method of providing such markers. The time constants during exhalation are plotted as a mathematical function which can be used to diagnose and monitor respiratory disease. The particle concentration with respect to time (i.e., the time constants) during exhalation from the lung is measured to provide a specific distribution function of the aerosol particles for each individual patient on a given day. The time constant data can then be stored or transmitted for comparison with data taken on a previous or future test.

Applicants envision that following an initial diagnosis by a physician with the apparatus of the invention, an asthmatic patient, for example, will be provided with the apparatus or variation of the apparatus to have in the home. The patient can then on a daily, weekly or monthly basis monitor their asthma through a self-test. The data collected from such tests can then be stored and/or transmitted to the physician (e.g., over the Internet).

One exemplary embodiment of the invention is shown in the schematic of FIG. 1. The arrows in FIG. 1 indicate the directions air can flow in each component of the apparatus. The dashed lines of FIG. 1 indicate static pressure lines, and the thin lines indicate an electronic attachment. The apparatus includes a multi-port coupling device 105a that couples with a detector 103a, a pressure device 107, an aerosol generator 106 and a computing device 109. A patient breathes through a mouthpiece (not shown) that is coupled to the detector 103a. It is to be understood that the configuration or position of each component in relation to the others, as shown in FIG. 1, is only one of a handful of possible configurations that can be used to practice the invention.

The multi-port coupling device 105a can be used to release an aerosol bolus produced by aerosol generator 106 into the air flow that is delivered to the patient. Alternatively, the aerosol bolus can be released into the air flow by the aerosol generator 106.

The aerosol generator 106 provides an aerosol bolus to be released at a determined point in a breathing cycle. Preferably, the aerosol bolus is mixed with the air flow during inhalation of air by the patient. The aerosol generator 106 can be any aerosol generation system known to those of ordinary skill that generates an aerosol with a particle size of from 0.05 microns to 1 micron, preferably from 0.1 microns to 0.8 microns, more preferably from 0.1 microns to 0.6 microns. For example, the aerosol generator can include a pressurized chamber which contains one or more substances that is to be aerosolized, and a nozzle with a select orifice diameter and shape.

The aerosol particles can include any relatively inert material that do not tend to aggregate within the patient, such that the particle size remains relatively constant as the particles are inhaled and exhaled from the patient's lungs. In one embodiment, the aerosol particles comprise one or more synthetic or natural oils, or a blend of natural and synthetic oils. The synthetic oil can include one or more fatty acids or, typically a blend of fatty acids. Most preferably, the aerosol comprises natural oil. An exemplary list of natural oils includes corn oil, canola oil, and oils derived from nuts. Neutral oils, for example, MIGLYOL, can also be used. The material used will also be labeled by any means of labeling known to those of ordinary skill that can be recognized electronically by the device so that no unauthorized material is aerosolized by the device. Examples include but are not limited to such identification means as bar codes, magnetic strips or eproms. Such identification would be encoded so as to be indecipherable by ordinary means.

In one embodiment, the aerosol generator 106 is coupled to the multi-port coupling device 105a so that the aerosol bolus is released into a chamber of the multi-port coupling device 105a.

In another embodiment, the aerosol generator 106 is connected to a chamber of the apparatus of the invention. In either case, the apparatus of the present invention is designed to release an aerosol bolus into the air flow at a determined point of a breathing cycle.

The detector 103a is used to measure the concentration of aerosol particles of a given volume in the air flow as the patient inhales and exhales. Any type of detector 103a known to those of ordinary skill that can measure particulate concentrations in a given volume can be used. Examples include but are not limited to light measuring devices such as photometers, photocells, mephelometers or photodiodes.

In one embodiment, as shown in FIG. 1, the pressure device 107 includes a filter 107a, a pneumotachagraph 107b, and a pressure transducer 107c. The pneumotachagraph 107b is used in conjunction with other components of the pressure measuring device 107 to determine the volume of air flow through the apparatus of the invention. The pneumotachagraph 107b measures a pressure differential across a fine mesh screen as air flows through the screen. The measured pressure differential is converted to an electronic signal by pressure transducer 107c coupled to pneumotachagraph 107b. The electronic signal can be digitized by an interface 109a included with computing device 109. The differential pressure data can be integrated with respect to time with computing device 109 to provide a volume of air flow for a plurality of respiratory cycles as well as the breathing cycle. The volume of air flow data can be stored for subsequent analysis. The computing device 109 will have the capability to collect, store, manipulate and display raw data, that is, data that is directly obtained from each component of the apparatus, as well as data that is generated by an algorithmic manipulation of the raw data.

The volume data collected refers to the amount of air a patient inhales and exhales from his or her lungs for a given respiratory cycle or breathing cycle. The apparatus of the invention has the capability to average the volume of air flow over any number of respiratory cycles. As a result, the apparatus and method of the invention can obtain ventilation data irrespective of the patient's respiratory condition at any given time or on any given day.

For example, the apparatus can obtain important ventilation data from an asthmatic that is experiencing extreme difficulty in breathing on a particular day, which is not possible with spirometry. Spirometry, which relies on a single respiratory cycle, can only tell the physician what he or she already knows, that is, the patient is having difficulty breathing. Also, the apparatus and method of the invention is more suited to collecting ventilation data from pediatric patients because a child can breath normally because there is no forced or directed breathing as required with spirometry.

The release of an aerosol bolus at a point in a breathing cycle, and the subsequent measurement of aerosol particle concentration with time, provides the physician with information on the upper respiratory tract of a patient. The collection of volume data allows the apparatus and method of the invention to determine at what point the aerosol bolus should be released into the air flow. In a preferred method of the invention, the aerosol bolus is released into the air flow at some point of an inhalation step of a respiratory cycle. This allows a greater dispersion of aerosol particles in the bronchi or upper region airways of the lungs where the obstruction(s) resulting from asthma or emphysema are typically located. This is an important feature because respiratory diseases such as asthma and emphysema affect the upper bronchi of lungs.

The measurement of time constants of aerosol particles and the amount of aerosol retained on any given breath as the aerosol moves just pass the obstruction or restriction and out again provides a very sensitive measurement of lung ventilation. The apparatus of the invention thus provides the physician with accurate and reliable information about the location of disease in the respiratory tract, whereas other known techniques such as spirometry are relatively insensitive in this regard.

Figure 2:
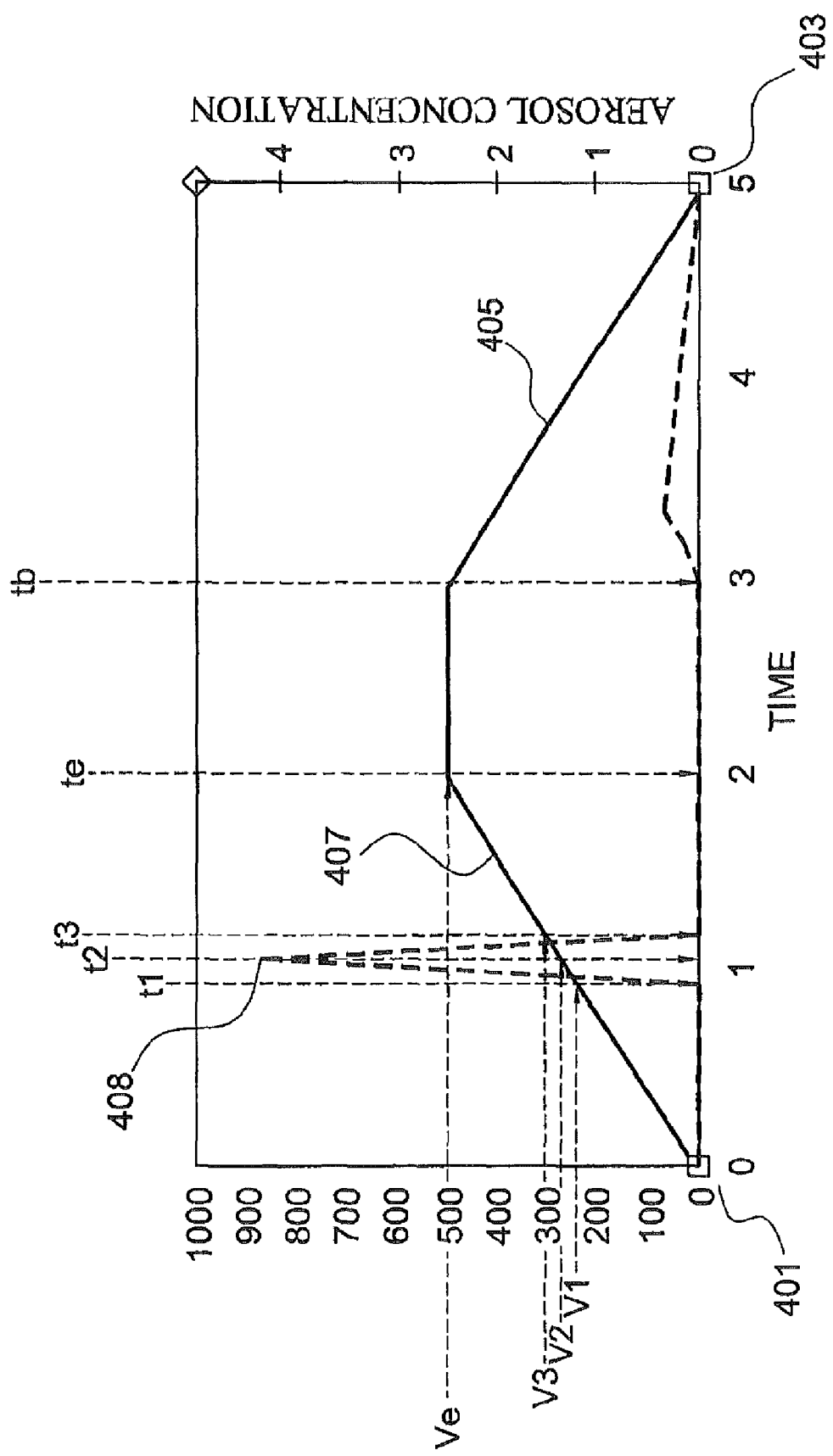
FIG. 2 depicts an exemplary representation of volume and concentration data.

A graphical representation of volume and aerosol particle concentration data shown in FIG. 2 describes an exemplary way in which the apparatus and method of the invention collects and analyzes data. FIG. 2 shows the aerosol particle concentration and volume data for a given inhalation and exhalation, i.e., a respiratory cycle in which an aerosol bolus is released into the air flow. The aerosol particle concentration is plotted as a function of time and is depicted as a dashed line. The time T1 corresponds to the time in the respiratory cycle that the aerosol bolus is released into the air flow. The peak volume 408 of the aerosol bolus occurs at time T2. The volume of air inhaled and exhaled by the patient is shown as the solid line. The rising portion of the volume data 402 with positive slope designates the inhalation step of the respiratory cycle. Likewise, the falling portion of the volume data 405 with a negative slope designates the exhalation step of the respiratory cycle. FIG. 2 uses arbitrary units of volume, time, and concentration to describe the coordinate axes.

The apparatus and method of the invention can be used to measure a particular volume of penetration $V_P$. The volume of penetration is defined as the volume of air inhaled following the release of an aerosol bolus into the airflow. To determine $V_P$, the apparatus requires that certain volume reference points be established. These reference points are volume of inhalation $V_1$ and total volume of inhalation $V_T$. Since the aerosol bolus has a measurable volume there are several equally valid reference points that can be used to determine the volume of inhalation. The volume of inhalation is the volume at which the aerosol bolus is released and may be defined in at least one of three ways: (1) the volume at which a signal is given or received to open a valve and let the aerosol enter the inhalation air stream; (2) the volume at which the concentration of particles rises above the background level by a given amount; or (3) the volume at which the concentration of particles rises for some specified rate for some specified period of time.

As shown in FIG. 2, $V_2$ is the midpoint of the aerosol bolus 408. $V_2$ is defined in one of three ways: (1) the centroid of the mass of the inhaled particle concentration; (2) the midpoint volume between the start and end volumes of the aerosol bolus ($[V_1+V_3]/2$); or (3) the volume at which the peak concentration of particles occurs. $V_3$ is defined as: (1) the volume at which a signal is given or received to close a valve and stop the flow of aerosol from entering the air flow; or (2) the volume at which the aerosol concentration drops to or below the background level. The preferred definition of $V_I$ is the midpoint volume. Further, the volume of penetration $V_P$ can be expressed as the difference between the average total volume of inhalation $V_T$ and the bolus inhalation volume $V_I$ (i.e., $V_P=V_T-V_I$).

As an example, in an adult asthma patient, typically it is only the last 50 cm$^3$ to 400 cm$^3$ of inhaled volume, more typically, 50 cm$^3$ to 200 cm$^3$ of inhaled volume, that provides the physician with important ventilation data. In a child, typically it is the last 25 cm$^3$ to 200 cm$^3$, more typically 25 cm$^3$ to 150 cm$^3$, of inhaled volume. In an infant, typically it is only the last 10 cm$^3$ to 100 cm$^3$, more typically 10 cm$^3$ to 50 cm$^3$ of inhaled volume. The term "adult" is defined as a person having reached the age of twelve. The term "child" is defined as a person between the ages of two and twelve. The term "infant" is defined as a newborn to the age of two.

The average total volume of inhalation can be determined prior to release of the aerosol bolus as the patient inhales and exhales through a mouthpiece of the apparatus. The digitized voltage of the pressure transducer is integrated to yield the volume of inhalation and exhalation irrespective of the total volume airflow. The method includes calculating an average volume of inhalation for any number of respiratory cycles before the aerosol bolus is released into the air flow. The average volume of inhalation can be stored in data storage 109. As the standard deviation of the running average of previous recorded volumes falls within a select value, the average inhalation volume is determined. Once the average inhalation volume is determined, the computing device 109 signals the multi-port coupling device 105 to release the aerosol into the air flow. Alternatively, the aerosol generator can release the aerosol directly into the air flow.

The pressure data is integrated with respect to time by the computing device 109. Consequently, any electronic noise or voltage offset that occurs during this time results in an error that should be corrected. This error is commonly referred to as "zero signal drift" or "volume drift", and accounts for differences in recorded volume/time data, which can be negative or positive differences, even if there is no air flow passing through the system. If this error component is significant and not accounted for the apparatus could interpret the volume drift as air flow that occurs during a breathing cycle. This volume drift could then cause errors in the measurement of volumes, and result in incorrect timing for the release of the aerosol bolus into the air flow.

Figure 3A:
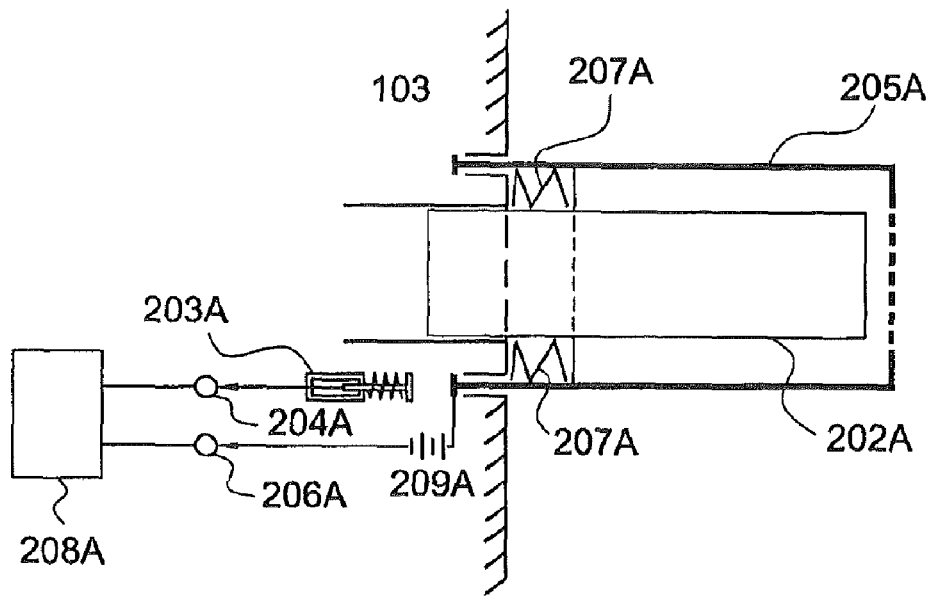
FIG. 3a shows a cut-away view of an exemplary mouthpiece in the non-active position for controlling volume drift.
Figure 3B:
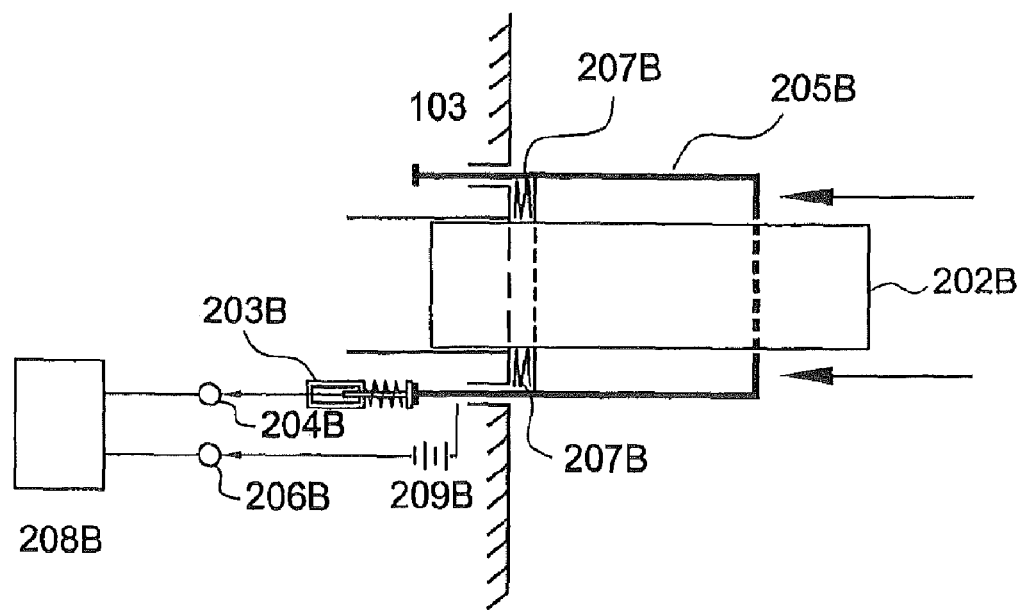
FIG. 3b shows a cut-away view of the mouthpiece of FIG. 3a in the active position for controlling volume drift.

In one embodiment, the apparatus includes a means for compensating for volume drift. For example, the apparatus can have the capability of digitally adding or subtracting values to and from the pressure flow signal from the pneumotachagraph 107*b* to nullify any error due to noise, thus maintaining a net volume drift of zero, FIG. 3*a* and FIG. 3*b* show a cut-away view of an exemplary means for controlling volume drift in the form of a volume drift control switch 201a, 201b. A cut-away view of a volume drift control switch that is not activated and a volume drift control switch 201b that is activated is shown in FIG. 3a and FIG. 3b, respectively.

The apparatus of the present invention can also include a sensor switch 203. The sensor switch 203 is coupled to the computing device 109, and communicates with computing device 109 as to initiation of a test or when data collection should begin. In one embodiment, a sensor switch 203a, 203b can be installed in the volume drift control switch 201a, 201b. For example, if the sensor switch 203a is not activated or in the open position, the signal from the pressure transducer 107c is not integrated and the volume drift remains uncorrected. However, if the sensor switch 203b is activated or in the closed position, the signal from the pressure transducer 107c is integrated to calculate volume data and the volume drift is corrected. In one embodiment, the sensor switch can include a toggle or button switch that remains closed as long as the switch is held in the closed position.

Figure 3C:
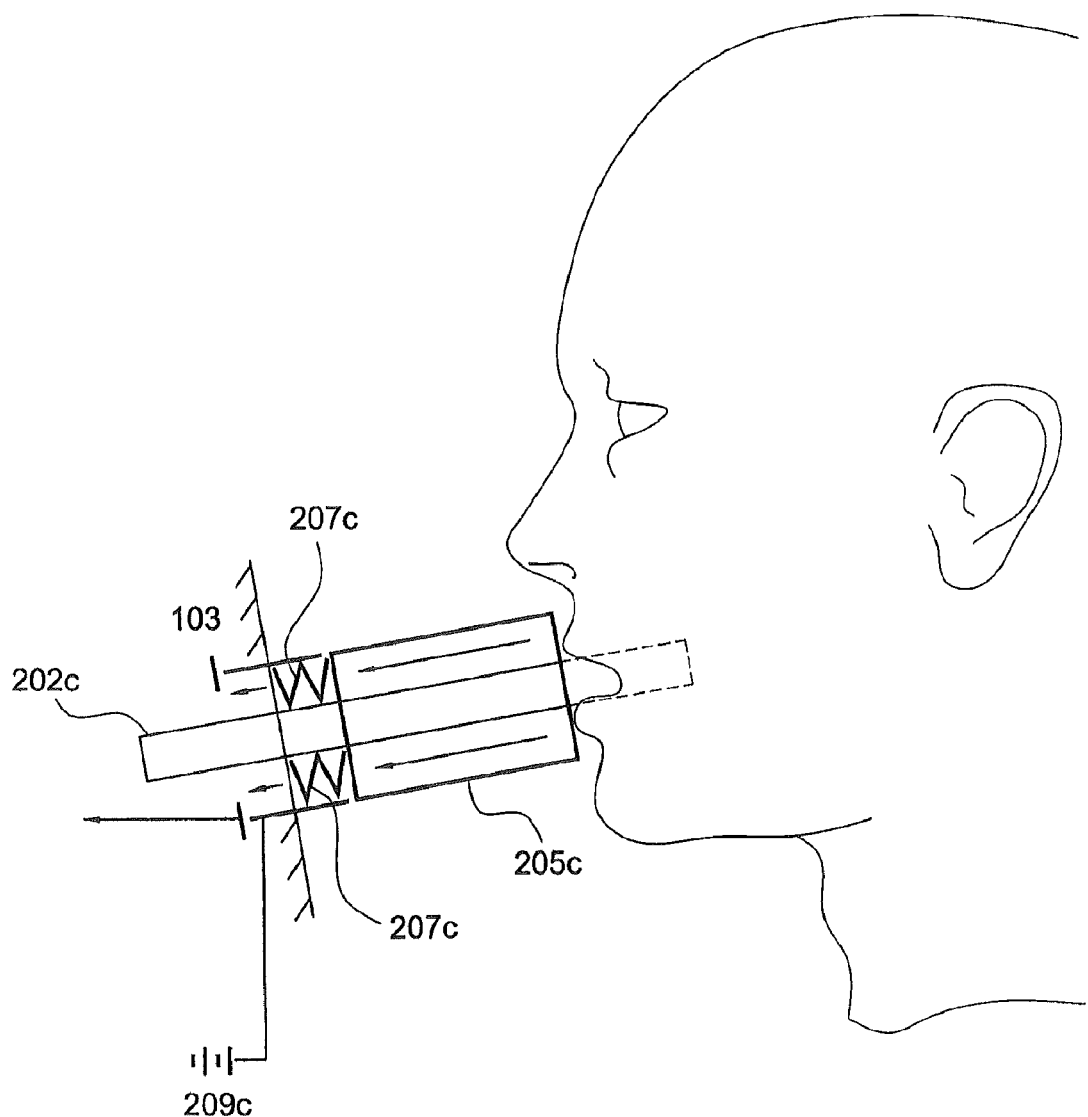
FIG. 3c shows a cut-away view of the mouthpiece of FIG. 3a for controlling volume drift in used by a patient.

In another exemplary embodiment, the sensor switch 201 is a retractable covering 205 for a mouthpiece 202, as shown in FIGS. 3a and 3b. In FIGS. 3a and 3b, the retractable covering 205 is a hollow tube open at both ends that can be retracted exposing the mouthpiece 202 by pushing against the retractable covering 205. The patient's lips push against the retractable covering 205 while inserting the mouthpiece 202 into their mouth. FIG. 3c shows an example of the volume drift control switch 200 with the subject 101 inserting the mouthpiece 202 into their mouth while pushing against the retractable covering 205 and activating the sensor switch 203. Activation of the sensor switch 203 occurs when the retractable covering 205 completes a circuit 204 by closing the sensor switch 203. An audible or visual sensor indicator signal can then be enabled by the circuit 204 to give an audible or visual sign that the sensor switch 203 has been activated and the test can begin. Upon removal of the mouthpiece from the mouth, a coil or spring 206 allows the retractable covering 205 to return to its original position.

In yet another exemplary embodiment, the sensor switch further comprises a proximity sensor that is used to determine when to stop signal averaging of a zero flow signal. The proximity sensor comprised of at least an electromagnetic wave source or transmitter of any wavelength with a matched receiver and shall be used to determine the proximity of a user to the aerosol dispersion device. The electromagnetic wave source is associated with the mouthpiece and shall transmit electromagnetic waves that shall be reflected from the body of the user back to the receiver that is also associated to the mouthpiece. The receiver shall be positioned at an angle of less than 90 degrees relative to the angle of the emitter. When the signal is received at the receiver, the computing device 109 shall cease averaging the pressure signal used to determine flow. In a preferred embodiment, the average pressure value is determined for the previous five seconds, but does not count the last second before the signal is received by the receiver, as the average zero pressure value. In addition, longer or shorter durations may be used for averaging times since the value is programmable. Changes in pressures encountered as long as the receptor is receiving emissions of electromagnetic waves shall be considered as due to flow and shall be integrated to determine the volume inhaled or exhaled by the user of the aerosol dispersion device. In a preferred embodiment the receiver and the transmitter shall be positioned in close proximity to one another and shall be in close proximity to the face of the user when the aerosol dispersion device is being used as intended.

Figure 4A:
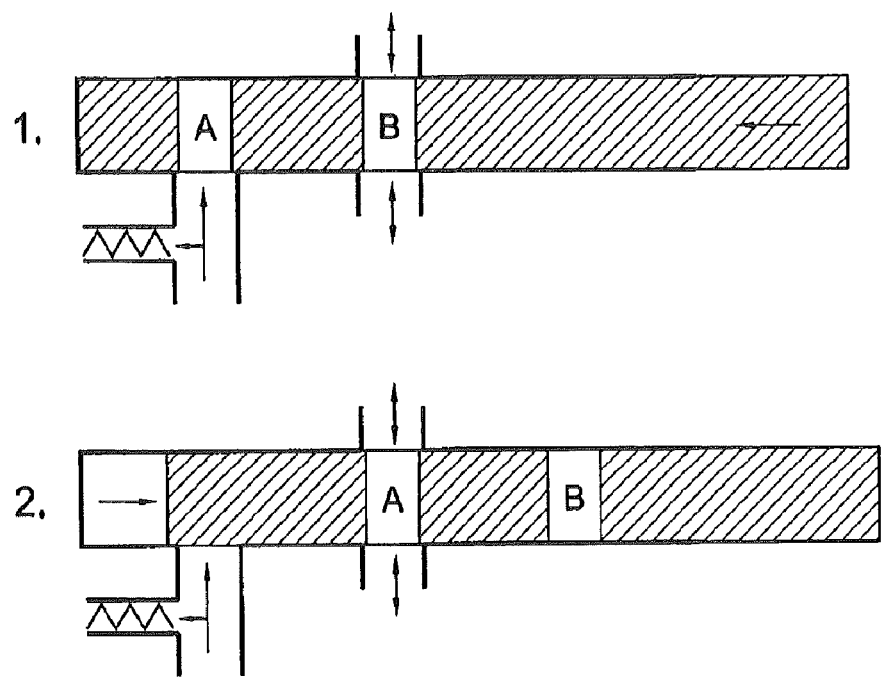
FIG. 4a is a top view of the two sections of an exemplary 3-way valve.
Figure 4B:
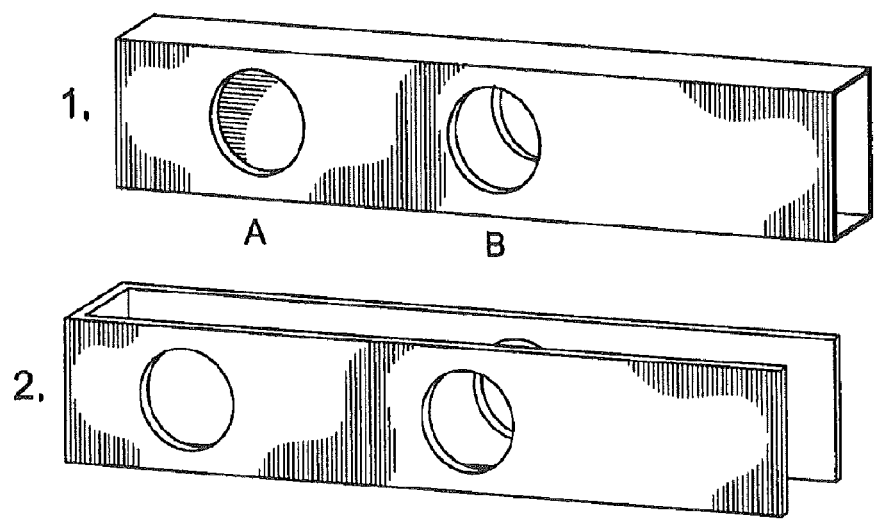
FIG. 4b is a front view of the two sections of an exemplary 3-way valve.
Figure 7:
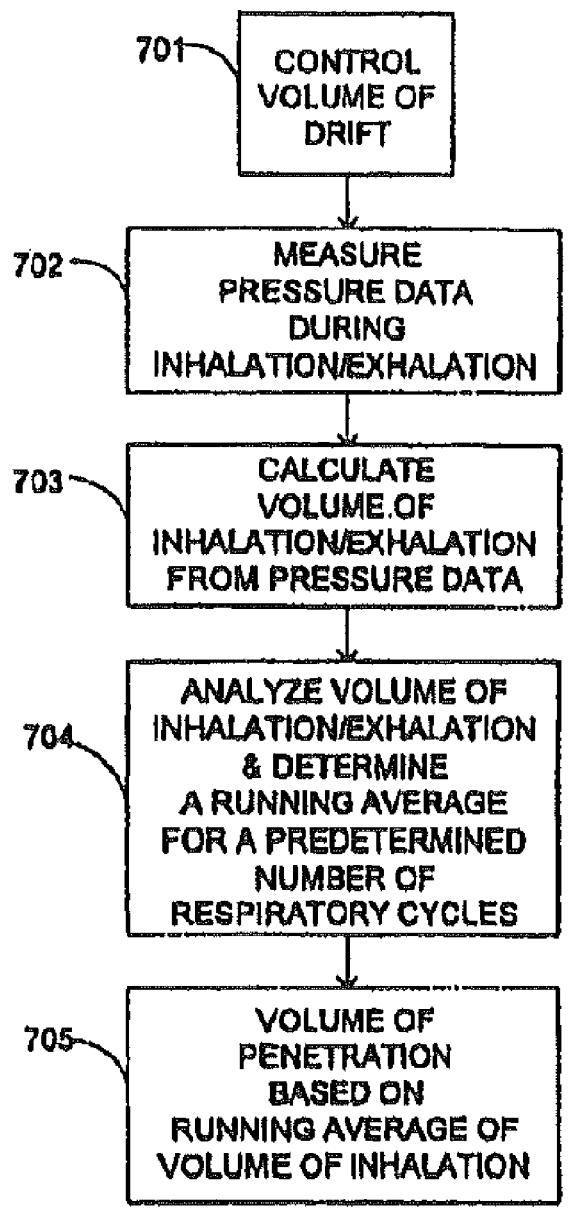
FIG. 7 shows an exemplary flow diagram for a method for providing a volume of penetration.
Figure 8:
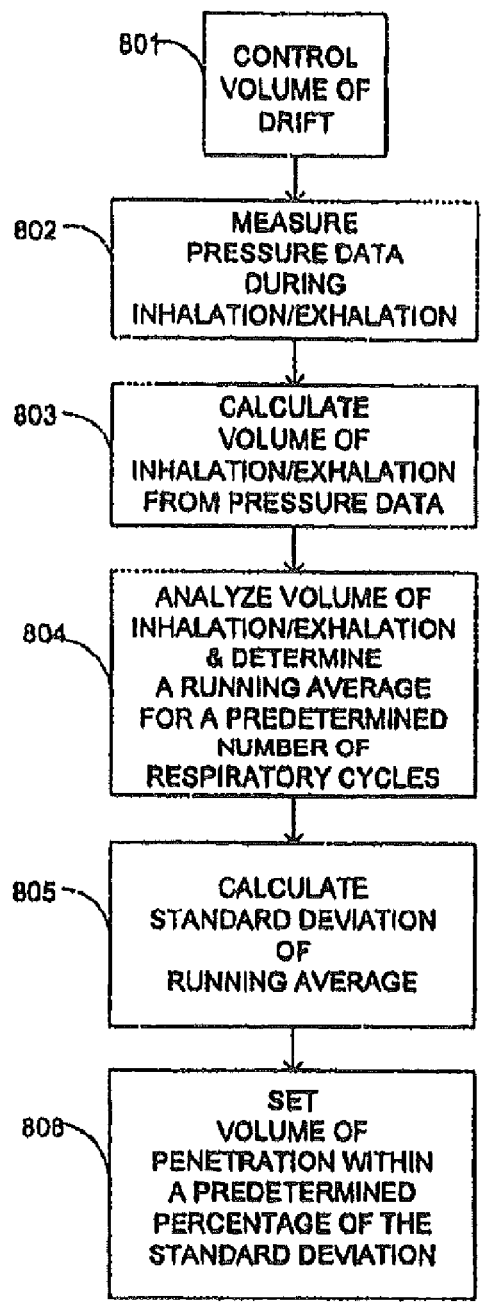
FIG. 8 shows another exemplary flow diagram for a method for providing a volume of penetration.

In yet another exemplary embodiment, the multi-port coupling device 105 is a 3-way valve, as shown in FIG. 4a. The 3-way valve 105a is coupled to the mouthpiece with detector 103, pressure device 107, and computing device 109. The 3-way valve is comprised of at least two sections as shown in. FIG. 4b.

When it is determined that an aerosol bolus needs to be injected into the breathing stream of the patient the valve system goes into the Delivery Mode, as shown in FIG. 4c. In this mode, the 3-way valve 3 is actuated to stop the flow of the gas into the piston chamber 4 and the valve 3 is opened to the atmosphere so that the pressure inside the piston chamber 4 is released. With the pressure released, the piston 5 is pushed back by the action of the spring 8 against the slider section 9 which slides freely against the piston. The spring 8 and the two chambers (A and B) in the slider are sized, so that the holding chamber A, filled with aerosol is positioned in the breathing stream of the patient. While the patient continues breathing a pulse or bolus of aerosol is delivered to the patient's lungs.

In the "Delivery Mode," as shown in FIG. 4c, the valve 9 acts to safeguard the subject from an accidental exposure to large volumes of high pressure gas which, if not controlled, could damage the subject's lungs. There is a double protection mechanism in this configuration because the holding chamber A can not be moved into the breathing stream until the valve 3 from the high pressure gas is closed. In addition, even if the valve 3 would fail or the pressure regulator 2 would fail the holding chamber is not connected to the pressurized portion of the system when the patient is breathing from it.

When in a "Filling Mode," the 3-way valve, as shown in FIG. 4d, consists of a gas source 1, e.g. carbon dioxide that is regulated, by a pressure regulator 2 through which the gas passes to a three-way valve 3 that can be actuated electronically to allow the gas to flow to a piston chamber 4. As gas flows into the piston chamber 4, movement of piston 5 provides passage of the gas into an aerosol nebulizer 6. As the gas flows into the nebulizer 6 an aerosol is generated. The generated aerosol flows into a holding chamber A in the slider section 9 of the 3-way valve, with any overflow being collected by a filter 7 which is open to the air. The filter may be located either, as shown in FIG. 4c, on the upstream side of the holding chamber A or on the downstream side of the holding chamber A (not shown), so that the generated aerosol passes through the holding chamber A on the way to the filter 7. In the filling mode, the slider section of the valve has been pushed against a spring 8 by the action of the piston 5. This allows aerosol to flow into the holding chamber A while a subject is able to breathe through an auxiliary chamber B that has been positioned in such a way as to be open to the air when the filling chamber A is being filled.

Methods described below can be used in association with the apparatus of the invention to determine the ventilating ability of a patient's lungs. Hereafter, these methods will be referred to as "Aerosol Bolus Dispersion" tests.

FIG. 5 shows an exemplary flow diagram for measuring the lung ventilation of a patient. The volume drift control switch 201 is activated (step 501). Pressure data is measured during respiratory cycles (step 502). The pressure data is converted to volume data following placement of the mouthpiece in the mouth (step 503) and saved in data storage 109b of computing device 109. A volume of inhalation is selected in step 504 to provide a known volume of penetration ($V_p$) given the total inhalation volume. Based on the $V_p$, a point in the breathing cycle, preferably during inhalation, is determined for the release of an aerosol bolus during (step 505). A detector 105 such as a photocell 105a is used to measure aerosol concentration during a plurality of respiratory cycles (step 507). The particle concentration during the respiratory cycle is used to calculate time constants (step 508). The particle concentration is then stored and available for display by the computing device 109 as a lung ventilation function (step 509).

FIG. 6 is a representative flow diagram of a second method for measuring lung ventilation with the apparatus of the invention. When the volume drift control switch 201 is activated, control of volume drift is initiated (step 601). Pressure data is measured during inhalation and exhalation (step 602). Calculations of the volume of inhalation and exhalation are made from the pressure data saved in data storage 109*b* of the computing device 109 (step 603). In particular, an analysis of the volume of inhalation is performed in step 604 to determine $V_p$. Based on the $V_p$, a time is determined for the injection of an aerosol bolus during inhalation (step 605). A light-measuring device, such as photocell 105*a*, detects the particles in the air flow during a number of respiratory cycles. The data is then stored in the data storage section 109*b* (step 606). The stored light data is analyzed by the computer 109 to determine the particle concentration during inhalation of each respiratory cycle (step 607). The particle concentration during each inhalation determined in step 607 is then used to predict the particle concentration (i.e., time constants) for each respective exhalation for a given respiratory cycle (step 608). The predicted particle concentration is stored and available for display by the computing device 109 as the predicted lung ventilation (step 609). The particle concentration for each exhalation is also measured and calculated for later comparison with the predicted value. Lung ventilation is measured by comparing the predicted distribution of time constants during exhalation (i.e., predicted from the particle concentration during inhalation) with the measured distribution of time constants during exhalation (step 610). The predicted and measured particle concentration data (i.e., time constants) is stored and available for display by the computing device 109 as the predicted lung ventilation (step 611). The physician is then able to make diagnosis based on any discrepancies between the predicted and measured particle concentrations/time constants.

FIG. 7 shows an exemplary flow diagram for a method for automatically controlling volume of penetration ($V_p$). When the volume drift control switch 201 is activated, control of volume drift is initiated (step 701). Pressure data is measured during inhalation and exhalation in step 702. Calculations of the volume of inhalation and exhalation are made from the pressure data saved in data storage 109*b* (step 703). The volume of inhalation data is used to determine the running average value of the volume of inhalation for a predetermined number of respiratory cycles (step 704). Based on this running average of the volume of inhalation, the $V_p$ is determined (step 705).

FIG. 8 shows another exemplary flow diagram for a method for automatically controlling volume of penetration ($V_p$). When the volume drift control switch 201 is activated, control of volume drift is initiated (step 801). Pressure data is measured during inhalation and exhalation (step 802). Calculations of the volume of inhalation and exhalation are made from the pressure data saved in data storage 109*b* (step 803). The volume of inhalation data is used is performed to determine a running average value of the volume of inhalation for a predetermined number of respiratory cycles (step 804). The standard of deviation of the running average is calculated (step 805). The $V_p$ is determined by setting the within a predetermined percentage of the standard deviation of the running average value of the volume of inhalation.

A mathematical model for the system function $f$ is used to determine the exhaled particle concentration ($C_{out}$) from the saved inhalation particle concentration data for a given breathing cycle. Because the dependence of $C_{out}$ on the inhaled concentration $C_{in}$ is assumed linear, the system function is the exhaled concentration that is due to an inhaled concentration that mathematically corresponds to a delta or impulse function.

If t is the time since the inhalation of the delta function concentration into the lung and Q is the rate at which air is inhaled and exhaled, then $V=Qt$ is the volume of air inhaled up to the volume of penetration $V_p=Qt_p$. For $t \geqq t_p$, $V-V_p=Qt-V_p$ is the amount of air exhaled. If all the particles are exhaled (no deposition), the system function $f(V;V_p)$ for the volume of penetration $V_p$ satisfies:

$$\int_{V_p}^{\infty} f(V;V_p)\,dV=1. \tag{1}$$

In the general case, $c_{in}(V)$ is not a delta function but is spread out over the volumes V where $\tilde{V}_0 \leqq V \leqq \tilde{V}_1$. A consequence of this spreading is the particles inhaled at different times (or V) will have different volumes of penetration. If $V_{p0}$ is the volume of penetration for the particles inhaled midway at $$V = \frac{(\tilde{V}_0 + \tilde{V}_1)}{2},$$

then the volume of penetration for the other particles inhaled at V as a function of V is $$V_p(v) = V_{p0} - \left[V - \frac{(\tilde{V}_0 + \tilde{V}_1)}{2}\right];\ \tilde{V}_0 \le V \le \tilde{V} \tag{2}$$

The linear dependence of $c_{out}(V)$ on $c_{in}(V)$ in the general case can now be expressed using the system function $f(V;V_P(V'))$ and $c_{in}(V')$ $$\tilde{C}_{out}(V)=\int_{\tilde{V}_0}^{\tilde{V}_1} \tilde{C}_{in}(V') f(V-V';V_p(V'))\,dV' \tag{3}$$

Equation (3) models only mixing in the lung.

However, there is also mixing occurring in the pre-lung consisting of the machine, mouth, and larynx. This mixing occurs on inhalation as well as exhalation. Let $c_{in}(V)$ be the concentration of particles as measured by the machine for $V_1 \leqq V \leqq V_0$. Since the flow is unidirectional, the mixing in the pre-lung is modeled as a linear and translation invariant process relating $\tilde{C}_{in}(V)$ to $c_{in}(V)$ (Nauman and Buffham) as $$\tilde{c}_{in}(V)=L[c_{in}(V)]=\int_{V_0}^{V_1} c_{in}(V') K(V-V')\,dV', \tag{4}$$

where K(V) is the system function for the mixing in the pre-lung. To model K(V) accurately is difficult. Since the mixing in the pre-lung is small compared to the mixing in the lung, it is reasonable to try to focus on estimating the moments $V_R$ and $\sigma_R^2$ where $$V_R=\int V K(V)\,dV \text{ and } \sigma_R^2=\int (V-V_R)^2 K(V)\,dV, \tag{5}$$

where $V_R$ corresponds to the effective mixing volume of the pre-lung and $\sigma_R^2$ corresponds to the variance.

The concentration $c_{in}(V)$ measured by the machine is first processed using equation (4) and then the resulting concentration $\tilde{c}_{in}(V)$ is transformed using equation (3) to determine the particle concentration, $\tilde{c}_{out}(V)$, exiting the lung. As stated earlier, mixing also occurs in the pre-lung on exhalation. It is reasonable to use equation (4) to calculate the model prediction for the exhaled concentration $c_{out}(V)$ from $$c_{out}(V)=L[\tilde{c}_{out}(V)]. \tag{6}$$

The model for the system function is based on the 24 generation network model of the human lung devised by Weibel. The function $f(V;V_p)$ is rewritten in terms of the conditional probabilities $S_i(V;Vp)$ (i=1, 2, ..., 24) and the probabilities $\alpha_i(V_p)$ as $$f(V; V_p) = \sum_{i=1}^{24} \alpha_i(V_p) S_i(V; V_p), \qquad (7)$$

where $S_i(V; V_p)dV$ is the probability that a particle exits the lung in (V,V+dV) given that it started exhalation "near" the end of generation i-1, (i=1, 2, ..., 24) and $\alpha_i(V_p)$ is the fraction of particles that are located "near" the end of generation i-1. Near the end of generation i-1 soon will be explained. Consequently, $$\sum_{i=1}^{24} \alpha_i(V_p) = 1 \text{ and } \int_{V_p}^{\infty} S_i(V; V_p) dV = 1 \qquad (8)$$

Moreover, it will be shown below that the dependence of $S_i(V; V_p)$ on $V_p$ is $$S_i(V; V_p) = S_i(V - V_p). \qquad (9)$$

Using equation (9) in equation (7) allows equation (3) to be rewritten as $$\tilde{c}_{out}(V) = \sum_{i=1}^{24} \left( \int_{\tilde{V}_0}^{\tilde{V}_1} \tilde{c}_{in}(V') \alpha_i(V_p(V')) dV' \right) S_i\left(V - V_{p0} + \frac{\tilde{V}_0 + \tilde{V}_1}{2}\right). \qquad (10)$$

The construction of both $\alpha_i(V)$ and $S_i(V-V_p)$ is based on the following assumptions:
(1) The transit time $t_i$ through each generation i-1 (i=1, 2, ..., 24) both on inhalation and exhalation is a random variable and these random variables are statistically independent.
(2) The dimensional parameters in the residence time distribution with unit $T^\delta$ (T is time) are proportional to $\bar{t}^s$ where $\bar{t}$ is the expected time through generation i.

A large class of mixing in the lung will be modeled by the following discrete Bernoulli distribution. It is determined by $$g t_i = \frac{g V_i}{Q}$$

the expected time; the time the first particle exits generation i-1; and $\sigma^2 = pg^2 \bar{t}_i^2$, the variance of the distribution. $V_i$ is the volume of generation i-1. See the Weibel Table below for values of $V_i$. In order to study a larger class of problems, a geometric scale factor g is introduced to demonstrably indicate that the volume of each generation is $gV_i$. The parameters are therefore $t_i$, $\alpha$, g, and p with $\alpha$, g, and p non-dimensional constants to satisfy assumption (2). There are two residence times $t_{i1} = \alpha g \bar{t}_i$ and $$t_{i2} = \left(g + \frac{gp}{1-\alpha}\right) \bar{t}_i.$$

To satisfy the above conditions, the probability $f(t_i)$ (for generation i-1, i=1, 2, ..., 24) attached to these times is $$f(t_i) = \begin{cases} r_1 = \dfrac{p}{(1-\alpha)^2 + p}, & t_i = t_{i1} \\ r_2 = \dfrac{(1-\alpha)^2}{(1-\alpha)^2 + p}, & t_i = t_{i1}. \end{cases} \qquad (11)$$

Assuming that all particles enter the lung at the same time, the problem is to determine the distribution of particles in each generation of the lung after the additional amount of air $V_p$ is inhaled using the distribution given by equation (11). It is useful to change variable from the time t since the start of inhalation, to V=Qt, the volume of air inhaled. It is also useful to calculate the cumulative distribution that gives the fraction of particles that already exited each generation as a function of air inhaled V. It is then an easy calculation to determine the percentage of particles in each generation at the end of inhalation.

For example, let $I_1(V)$ be the fraction of particles that have exited generation zero as a function of air inhaled $V \geq 0$. Then, using equation (9) with i=1 gives $$I_1(V) = \begin{cases} 0, & 0 \leq V \leq V_{11}^T \\ r_1 & V_{11}^T \leq V < V_{12}^T \\ 1, & V_{12}^T < V \end{cases} \qquad (12)$$

The important points in the domain of $I_1(V)$ are $V_{11}^T = \alpha g V_1 = Q t_{11}$ and $$V_{12}^T = \left(g + \frac{gp}{1-\alpha}\right) V_1 = Q t_{12} \cdot g V_1;$$

is the volume of generation zero.

To calculate $I_2(V)$, the fraction of particles that have exited generation one as a function of V, use the assumption that the random variables $t_1$ and $t_2$ are independent. Initially, there are four critical values in the domain:

$$V_{21}^T = \alpha g(V_1 + V_2) = Q(t_{11} + t_{21})$$

$$V_{11} + V_{12} = \alpha g V_1 + \left(g + \frac{gp}{1-\alpha}\right) V_2$$

$$V_{21} + V_{22} = \alpha g V_2 + \left(g + \frac{gp}{1-\alpha}\right) V_1$$

$$V_{22}^T = \left(g + \frac{gp}{1-\alpha}\right)(V_1 + V_2) = Q(t_{12} + t_{22})$$

The definition of $\tilde{I}_2$ (the tilde to be explained) is $$\tilde{I}_2(V) = \begin{cases} 0, & 0 \leq V < V_{21}^T \\ r_1^2, & V_{21}^T \leq V < V_{11} + V_{22} \\ r_1^2 + r_1 r_2, & V_{11} + V_{22} \leq V_{21} + V_{12} \\ r_1^2 + 2 r_1 r_2, & V_{21} + V_{12} \leq V < V_{22}^T \\ 1, & V_{22}^T \leq V. \end{cases}$$

Observe that the average value of $V_{11}+V_{22}$ and $V_{21}+V_{12}$ in the domain of $\tilde{I}_2$ is midway between $V_{21}^T$ and $V_{22}^T$. A reasonable simplification is to attach the probability $r_1^2+2r_1r_2$ to this midpoint and thus group together the two similar paths the corresponding particles in the lung have traveled. This resulting function is written $I_2(V)$ and given as $$I_2(V) = \begin{cases} 0, & 0 \leq V < V_{21}^T \\ r_1^2, & V_{21}^T \leq V < V_{21}^T + \frac{V_{22}^T - V_{21}^T}{2} \\ r_1^2 + r_1 r_2, & V_{21}^T + \frac{V_{22}^T - V_{21}^T}{2} \leq V < V_{22}^T \\ 1, & V_{22}^T \leq V \end{cases} \quad (13)$$

The function $I_i(V)$ (i=1, 2, . . . , 24) is the fraction of particles that have exited generation i-1 as a function of V and is calculated using independence of random variables $t_i$, the distribution in equation (11), and as done in the definition of $I_2$, grouping together all paths that have probability $r_1^{i-k} r_2^k$ for k=0, 1, . . . , i. It can be shown that the average value of V where these particles exit generation i-1 is $$V_{i1}^T + \frac{k \Delta V_i}{i}$$

where $$V_i^T = V_1 + V_2 + \cdots + V_i$$
$$V_{i1}^T = \alpha g$$
$$V_{i2}^T = \left(g + \frac{gp}{1-\alpha}\right) V_i^T$$
$$\Delta V_i = V_{i2}^T - V_{i1}^T$$

There are $$\frac{i!}{k!(i-k)!}$$

such paths with probability $r_1^{i-k} r_2^k$. Thus, the definition of $I_i$ is $$I_i(V) = \begin{cases} 0, & 0 \leq V < V_{i1}^T \\ r_1^i, & V_{i1}^T \leq V < V_{i1}^T + \frac{\Delta V_i}{i} \\ r_1^i + \frac{i!}{1!(i-1)!} r_1^{i-1} r_2, & V_{i1}^T + \frac{\Delta V_i}{i} \leq V < V_{i1}^T + \frac{2 \Delta V_i}{i} \\ \cdots \\ \sum_{j=0}^{k} \frac{i!}{j!(i-j)!} r_1^{i-j} r_2^j, & V_{i1}^T + \frac{k \Delta V_i}{i} \leq V < V_{i1}^T + \frac{(k+1)\Delta V_i}{i} \\ \cdots \\ 1, & V_{i2}^T \leq V \end{cases}$$

The grouping together of paths reduced the number of jumps in $I_i(V)$ from $2^i$ to i+1, a considerable savings in accounting with an acceptable loss in accuracy. Finally, $I_0(V)$ is defined to be 1 for all $V \geq 0$ and corresponds to all particles entering the system immediately. Putting $V=V_{p0}$ will emphasize that $I_i(V_{p0})$ corresponds to the distribution of particles at the end of inhalation.

Fortunately, it is possible to further simplify the expression for $I_i(V_{p0})$ using $$I_i \approx \sum_{j=0}^{k} \frac{i!}{k!(i-k)!} r_1^{i-k} r_2^k \approx \frac{1}{\sqrt{2 \pi i r_1 r_2}} \int_{-\infty}^{k} e^{-(x-ir_2)^2/2ir_1 r_2} dx \quad (14)$$

In order to change to the continuous variable $V_{p0}$ in equation (14) from the integer variable k use the equations $$V_p(x) = V_{i1}^T + \frac{x \Delta V}{i}$$

and $V_p(k) = V_{p0}$:

$$I_i(V_{p0}) = \frac{1}{\sqrt{2 \pi \sigma_i^2}} \int_{-\infty}^{V_{p0}} e^{-(x - V_{i1}^T - r_2 \Delta V_i)^2/2\sigma_i^2} dx$$

where $$\sigma_i^2 = \frac{r_1 r_2 (\Delta V_i)^2}{i}.$$

Letting $$y = \frac{x}{g V_i^T}$$

and replacing $r_1$, $r_2$, and $\Delta V_i$ with their equivalent in terms of $\alpha$, g, p, and $V_i^T$ gives $$I_i\left(\frac{V_{p0}}{g}; p\right) = I_i(V_{p0}) = \frac{1}{\sqrt{\frac{2\pi p}{i}}} \int_{-\infty}^{V_{p0}/g V_i^T} e^{-(y-1)^2/\frac{2p}{i}} dy, \quad (15)$$

$i = 1, 2, \cdots, 24$

The notation for $I_i$ has changed to show the dependence on the parameters g and p in addition to $V_{p0}$. Note that, with the approximation given by equation (14), the dependence on $\alpha$ is gone. The definition of $I_0(V_p)$ remains unchanged.

Since $I_i$ gives the fraction of particles that have exited generation i-I (i-1=1, 2, . . . , 23), the fraction of particles in generation i-I at the end of inhalation is $q_i = I_{i-1} - I_i$. The fraction of particles beyond generation 23 is given by $q_{25} = I_{24}$.

To calculate how the particles exit the lung, first assume that all the particles in the deeper half of generation i-I and shallower half of generation i are all located at the end of generation i-1. This is the definition of $\alpha_i$ for i=1, 2, . . . , 23. $\alpha_{24}$ includes all the particles in the deeper half of generation 23 and beyond. This accounts for all the particles in the lung except for the particles in the shallower half of generation zero, which should be negligible for the useful values of $V_{p0}$. The explicit formulas are (i.e., letting $x = y - 1/\sqrt{p/i}$ in equation (15))

$$\alpha_1\left(\frac{V_{p0}}{g}, p\right) = \frac{1}{2\sqrt{2\pi}} \int_{\left(\frac{V_{p0}}{gV_2^T}-1\right)/\sqrt{\frac{p}{2}}}^{\infty} e^{-x^2/2} dx$$

$$\alpha_i\left(\frac{V_{p0}}{g}, p\right) = \frac{1}{2\sqrt{2\pi}} \int_{\left(\frac{V_{p0}}{gV_{i+1}^T}-1\right)/\sqrt{\frac{p}{i+1}}}^{\left(\frac{V_{p0}}{gV_{i-1}^T}-1\right)/\sqrt{\frac{p}{i-1}}} e^{-x^2/2} dx$$

$$i = 2, 3, \cdots, 23$$

$$\alpha_{24}\left(\frac{V_{p0}}{g}, p\right) = \frac{1}{2\sqrt{2\pi}} \int_{-\infty}^{\left(\frac{V_{p0}}{gV_{23}^T}-1\right)/\sqrt{\frac{p}{23}}} e^{-x^2/2} dx$$

The construction of the conditional probabilities $S_i(V; V_p)$ is similar to $\alpha_i(V)$. This yields $$S_i(V; V_p) = S_i(V - V_p, g^e, p^e) = \frac{1}{g^e V_i^T \sqrt{\frac{2\pi i p^e}{(i+1)^2}}} e^{-\left(\frac{V-V_p}{g^e V_i^T}-1\right)^2 / \frac{2i p^e}{(i+1)^2}} \quad (17)$$

Note that the dependence of $S_i$ on $V$ and $V_p$ and is in the form $V - V_p$. The meanings of $g^e$ and $p^e$ are the same as used on inhalation. The value of $g^e$ is the geometric scale factor for the volume of the lung on exhalation and $p^e$ is the variance factor. The corresponding factors on inhalation will now be written as $g^i$ and $p^i$.

The first and second moments of the random variable $y_i$ with distribution $S_i(y, g^3, p^e)$ will be important for theoretical reasons and for estimating parameters from experimental data. These moments are $$E(y_i) = g^e V_i^T \text{ and } E(y_i^2) = (g^e V_i^T)^2\left(1 + \frac{i p^e}{(i+1)^2}\right) \quad (18)$$

The system function for mixing in the lung can now be written as (see equation (7))

$$f(v; V_p, g^i, p^i, g^e, p^e) = \sum_{i=1}^{24} \alpha_i\left(\frac{V_p}{g^i}, p^i\right) S_i(V - V_p, g^e, p^e)$$

It can be demonstrated through simulation of $f$ for the reasonable range of parameter values that for a factor $r$ of order 1

$$f(V; V_p, rg^i, p^i, rg^e, p^e) = f(V; V_p, g^i, p^i, g^e, p^e)$$

Letting $r = (g^i)^{-1}$ $$f\left(V; V_p, 1, p^i, \frac{g^e}{g^i}, p^e\right) = f(V; V_p, g^i, p^i, g^e, p^e) \quad (19)$$

The model shows that the exhaled concentration from the lung contains information only on the relative effective volume $g^3/g^j$ in addition to $p^i$ and $p^e$.

In view of the mixing in the prelung with volume $V_R$ (see equation (5)), equation (2) becomes $$V_p(V) = V_{p0} - \left(V - \left(\frac{V_0 + V_1}{2} + V_R\right)\right) \quad (20)$$

with $$\frac{\tilde{V}_0 + \tilde{V}_1}{2} = \frac{V_0 + V_R + V_1 + V_R}{2}.$$

Consequently, equation (10) becomes $$\tilde{c}_{out}\left(V, \frac{g^e}{g^i}, p^i, p^e; V_{p0}\right) = \sum_{i=1}^{24} \int_{\tilde{V}_0}^{\tilde{V}_1} \tilde{c}_{in}(V') \alpha_i(V_p(V'), p^i) \quad (21)$$

$$S_i\left(V - \left(V_{p0} + \frac{V_0 + V_1}{2} + V_R\right), \frac{g^e}{g^i}, p^e\right) dV'.$$

Using equation (21) in equation (6) gives the model prediction for the exhaled particle concentration measured by the apparatus as $$c_{out}\left(V, \frac{g^e}{g^i}, p^i, p^e; V_{p0}\right) = \int \tilde{c}_{out}\left(\tilde{V}, \frac{g^e}{g^i}, p^i, p^e; V_{p0}\right) K(V - \tilde{V}) d\tilde{V}. \quad (22)$$

The integration in equation (22) is over the interval where $\tilde{c}_{out}$ is nonzero.

It is clear from equation (22) that the parameters to be estimated include $$\frac{g^e}{g^i},$$

$p^i$, and $p^e$. $V_{po}$ is the average volume of penetration into the lung, whereas $V_{po} + V_R$ is the total volume of air measured by the apparatus at the end of inhalation. Thus $V_{po}$ will be known once $V_R$ is known or estimated.

Let $c_{out}^M(V_i)$ denote the actual exhaled concentration measured by the apparatus at the discrete values $V_i$, $i = 1, 2, \ldots, n$. Due to measurement noise, inadequacy of the model, etc, the relationship between the measured output and the model prediction is $$c_{out}^M(V_i) = c_{out}(V_i, \ldots) + \epsilon_i \quad (23)$$

At this stage, it is reasonable to use the minimum least squares criterion to estimate the parameters Minimize:

$$F\left(\frac{g^e}{g^i}, p^i, p^e; V_{p0}\right) = \sum_{i=1}^{n} \left(c_{out}^M(V_i) - c_{out}\left(V_i, \frac{g^e}{g^i}, p^i, p^e; V_{p0}\right)\right)^2. \quad (24)$$

It is useful to calculate the first two moments of the model prediction $c_{out}(V, \ldots)$ $$E(V) = \int V c_{out}(V, \ldots) dV / \int c_{out}(V, \ldots) dV$$

$$E(V - E(V))^2 = \int (v - E(V))^2 c_{out}(V, \ldots) dV / \int c_{out}(V, \ldots) dV$$

A direct calculation of E(V) using equation (22) gives $$E(V) = V_{p0} + 2V_R + \frac{V_0 + V_1}{2} + \frac{g^e}{g^i} A_0(p^i) V_{p0} \quad (25)$$

Recall that the variable V is related to the volume of air through the machine with $$\frac{V_0 + V_1}{2}$$

(the center of the $c_{in}(V)$ distribution) playing the role of the origin. In arriving at 2 equation (25), the following approximation was used:

$$\sum_{i=1}^{24} \alpha_i(V_p, p^i) V_i^T \approx A_0(p^i) V_p \approx (1.00919 + 0.0688435 p^i) V_p$$

The important term in equation (25) is $$\frac{g^e}{g^i} A_0(p^i) V_{p0}.$$

It is approximately $V_{p0}$ corresponding to the additional volume within which the typical particle exits the lung given that the volume of penetration into the lung is $V_{p0}$. The model shows that this value is inflated by the intrinsic mixing occurring during inhalation (quantified by the parameter $p^i$) and the relative effective volume of the lung $$\frac{g^e}{g^i}.$$

The direct calculation of $E(V-E(V))^2$ gives $$E(V - E(V))^2 = \sigma_R^2 + \\ \left(\frac{g^e}{g^i}\right)^2 (B_0(p^i) + p^e B_1(p^i))(\sigma_R^2 + V_{p0}^2 + \sigma_{in}^2) - \left(\frac{g^e}{g^i}\right)^2 (A_0(p^i) V_{p0})^2; \quad (26)$$

where $\sigma_R^2$ is defined by equation (5) and $\sigma_{in}^2$ is the variance of the $C_{in}(V)$ distribution.

The functions $B_o(p^i)$ and $B_1(p^i)$ have derivations similar to $A_0(p^i)$:

$$\sum_{i=1}^{24} \alpha_i(V_p, p^i)(V_i^T)^2 \approx B_0(p^i) V_p^2;$$

and $$\sum_{i=1}^{24} \alpha_i(V_p, p^i) \frac{(V_i^T)^2 i}{(i+1)^2} \approx B_1(p^i) V_p^2.$$

The sample mean $\overline{V}$ and variance $\overline{(V-\overline{V})^2}$ are defined to be $$\overline{V} = \sum_{i=1}^{n} V_i c_{out}^M(V_i) \bigg/ \sum_{i=1}^{n} c_{out}^M(V_i);$$

and $$\overline{(V - \overline{V})^2} = \sum_{i=1}^{n} (V_i - \overline{V})^2 c_{out}^M(V^i) \bigg/ \sum_{i=1}^{n} c_{out}^M(V^i).$$

Therefore, in order to have initial estimates for $$\frac{g^e}{g^i},$$

$p^i$, and $p^e$, use the approximations $E(V) \approx \overline{V}$ and $E(V-E(V))^2 \approx \overline{(V-\overline{V})^2}$ in equations (25) and (26), and solve for $$\frac{g^e}{g^i} p^i = p^e = p$$

(assume $p^i = p^e$ for simplicity). Use these as starting values in the numerical procedures for minimizing $$F\left(\frac{g^e}{g^i}, p^i, p^e; V_{p0}\right)$$

defined in equation (24).

Figure 9:
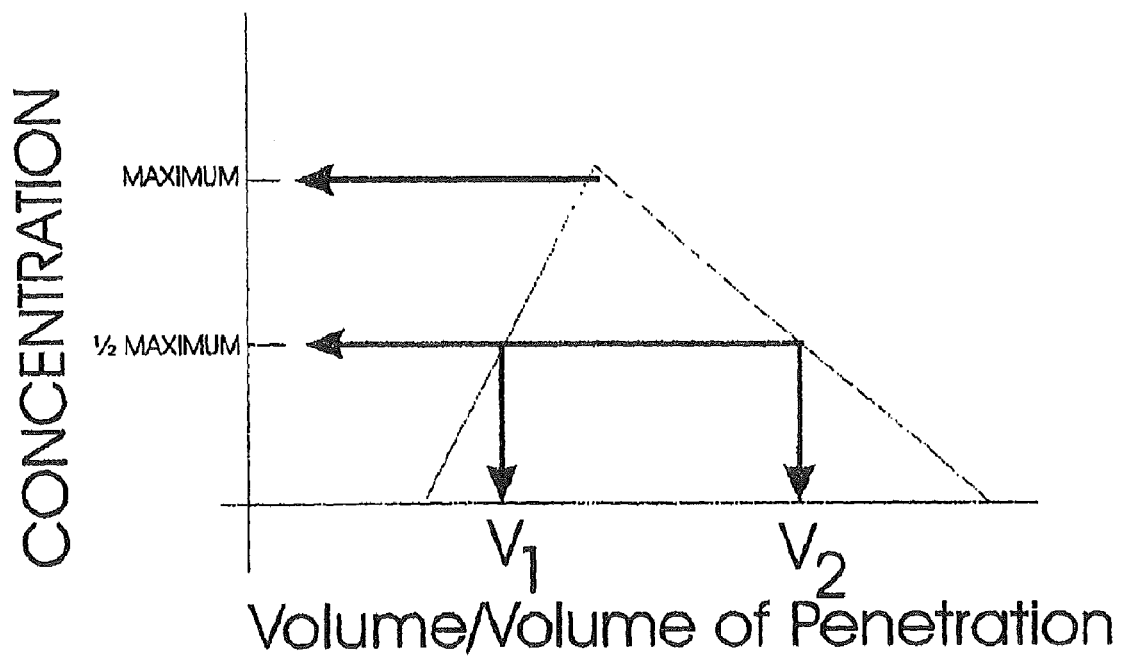
FIG. 9 depicts another exemplary representation of volume and concentration data.

As a non-limiting example of the method of the present invention, the exhaled aerosol concentration as a function of volume exhaled can be analyzed by determining the volume difference at half the peak concentration, as shown in FIG. 9. In this method, the volume exhaled is divided by the volume of penetration. At the volume at which half the peak concentration is reached and on the increasing slope side of the exhaled concentration profile, the initial volume value $V_1$ is obtained corresponding to the volume coordinate of that point. On the declining concentration side of the exhaled concentration profile the final volume value $V_2$ is obtained corresponding to the volume coordinate of the concentration point at which the concentration is half the maximum. The resultant measure of dispersion is therefore $V_2-V_1$. Since each volume value is divided by the volume of penetration, the expected result of $V_2-V_1$ should be approximately the same for all volumes of penetration as long as the bolus does not penetrate into the gas exchange region of the lung. Should the result of $V_2-V_1$ change in a statistically significant way when compared to previous differentials for smaller volumes of penetration, the volume of penetration at which that occurs will be deemed the appropriate volume for introduction of a therapeutic aerosol. The output of the apparatus is the concentration of aerosol $c_{out}$ as a function of volume exhaled V. These two variables can be related by three parameters as:

$$c_{out}(V, p^i, g, p^e) = \int_{-\infty}^{\infty} \tilde{c}_{out}(\tilde{V}, p^i, g, p^e) K(V-\tilde{V}) d\tilde{V} \tag{27}$$

where the three parameters are:

$p^i$, $p^e$=intrinsic mixing on inhalation and exhalation, respectively; and g=relative effective volume (i.e., the effective volume of lung on exhalation $g^e$ divided by effective volume of lung on inhalation $g^i$).

These three parameters are determined by comparing the output from the above Equation (27) to the actual data for various values of the parameters. This is done at a given volume of penetration $V_{p0}$.

Equation (27) is derived by the following method:
a. $c_{out}(V, p^i, g, p^e)$ is compared to the actual data from the apparatus;
b. $c_{in}(V)$=concentration of particles as a function of total volume measured by the apparatus upon inhalation, where $(V_i \leq V \leq V_r)$; and
c. $\tilde{c}_{in}(V) = \int_{V_i}^{V_r} c_{in}(\tilde{V}) K(V-\tilde{V}) d\tilde{V}$, where K is to be determined.

One possibility for determining K is the expression:

$$K(V) = \frac{1}{\sqrt{2\pi}\sigma_R} e^{-\frac{(V-V_R)^2}{2\sigma_R^2}},$$

where $V_R$ is the effective volume of the prelung, and $\sigma_R$ is the standard deviation of mixing in the prelung.

In addition, $c_{out}$ is approximately:

$$\tilde{c}_{out}(V, p^i, g, p^e) = \sum_{i=1}^{24} \left( \int_{-\infty}^{\infty} \tilde{c}_{in}(V') \alpha_i(V_p(V'), p^i) dV' \right) S_i\left(V - \left(V_{p0} + V_R + \frac{V_l + V_r}{2}\right), g, p^e\right)$$

where:

$$V_p(V') = V_{p0} + V_R + \frac{V_l + V_r}{2} - V';$$

$V_{p0}$ = volume of penetration for particles at $\frac{V_l + V_r}{2}$;

$V_i$=volumes from Weibel's table (see below) i=1, 2, ..., 24, $V_{i\infty}^T = V_1 + V_2 - \ldots + V_i$;

$$\alpha_1(t, p^i) = \frac{1}{2\sqrt{2\pi}} \int_{\left(\frac{t}{V_{2\infty}^T}-1\right)/\sqrt{\frac{p^i}{2}}}^{\infty} e^{-x^2/2} dx, \text{ at } i = 1;$$

$$\alpha_i(t, p^i) = \frac{1}{2\sqrt{2\pi}} \int_{\left(\frac{t}{V_{i\infty}^T}-1\right)/\sqrt{\frac{p^i}{i+1}}}^{\left(\frac{t}{V_{i-1\infty}^T}-1\right)/\sqrt{\frac{p^i}{i-1}}} e^{-x^2/2} dx,$$

i = 2, 3, ... , 23;

$$\alpha_{24}(t, p^i) = \frac{1}{2\sqrt{2\pi}} \int_{-\infty}^{\left(\frac{t}{V_{23\infty}^T}-1\right)/\sqrt{\frac{p^i}{23}}} e^{-x^2/2} dx, \text{ at } i = 24;$$

and $$S_i(y; g, p^e) = \frac{1}{gV_{i\infty}^T \sqrt{\frac{2\pi i p^e}{(i+1)^2}}} e^{-\left(\frac{y}{gV_{i\infty}^T}-1\right)^2 / \frac{2ip^e}{(i+1)^2}}.$$

Moreover, Weibel's Table discussed above is given by:

V(1) = 30.5
V(2) = 11.25
V(3) = 3.97
V(4) = 1.52
V(5) = 3.46
V(6) = 3.3
V(7) = 3.53
V(8) = 3.85
V(9) = 4.45
V(10) = 5.17
V(11) = 6.21
V(12) = 7.56
V(13) = 9.82
V(14) = 12.45
V(15) = 16.4
V(16) = 21.7
V(17) = 29.7
V(18) = 41.8
V(19) = 61.1
V(20) = 93.2
V(21) = 139.5
V(22) = 224.3
V(23) = 350.0
V(24) = 591.0

While the above derivations were performed for an aerosol concentration as a function of time at a constant flow rate, it should be noted that both time and volume are interchangeable. Thus, volume and dimensionless volume (i.e., the volume of inhalation divided by the average volume inhaled), could be used in place of time in the above derivation. To illustrate this concept, a time domain derivation of another element of the invention is presented below.

When analyzing the response curves obtained for subjects inhaling aerosol boluses, background art methods did not account for the non-symmetry of the response curves in their mathematical treatments. This non-homogeneity of ventilation is not only associated with diseased subjects but also with healthy subjects as well. Therefore, mathematical models for the present method of the present invention were designed to treat mixing in both diseased and healthy subjects and typically include a term for the non-homogeneity of ventilation.

The above observations provide for a model formulation beginning with a hypothetical mixing chamber in which the extent of mixing could be varied. Models of background art methods have used the simplifying assumption of a Guassian shape for the response curves exhalation profile. However, the present invention considers the response curves to be non-Guassian (i.e., asymmetric). The appearance of these non-symmetric response curves is strikingly similar to a Gamma distribution. Such a distribution is commonly used to model mixing in stirred reaction vessels. A system of such reaction vessels, when modeled appropriately, results in the following expression for the exit concentration:

$$E(t) = \frac{p^p}{\bar{t}^p \Gamma(p)} t^{p-1} e^{\frac{-pt}{\bar{t}}} \qquad (28)$$

where: t=the exit age of a particle flowing through the system;
$\bar{t}$=the mean residence time of the particles in the system;
E(t)=the outlet concentration for a given unit impulse of a pulsed tracer; and
$\Gamma$=the gamma function=$\Gamma(p)$=(p−1)!

Equation (28) is generally referred to as the "tanks-in-series model," in which p is the number of reactors in series. When p=1, the distribution is exponential and is the standard distribution expected for a single stirred-tank reactor. As p approaches infinity, the exit time for all the particles becomes the same, thus approaching a plug-flow condition. For this extreme, the response becomes increasingly steeper and approaches a normal distribution. This enables a comparison of the "tanks-in-series" model with other background art dispersion models. Such a comparison yields an important dimensionless measure, the Peclet number $N_{Pe}$), which is used to relate the contribution of the convective mixing over the mixing by dispersion. For large p, $N_{Pe}=2p$ and for small p, $N_{Pe}=2(p-1)$.

Another important feature of the Gamma Distribution model of Equation (28) is the potential to add a by-pass loop which accounts for that fraction of the aerosol bolus not penetrating the alveolar ducts. In addition, another term can be introduced that models the effect of increased regional time constants due to obstruction. This assumes that the upper airways contribute little to the overall ventilation in the lung. Therefore, any aerosol remaining in the upper airways basically by-passes the ventilation section (i.e., lower airways and alveoli) of the lung. This accounts for the parallel ventilation. A gamma distribution with a by-pass loop is given in Equation (28) as:

$$E(t)_\Gamma = \frac{(p\beta)^p}{\bar{t}^p\Gamma(p)}t^{(p-1)}e^{\frac{-p\beta t}{\bar{t}}} \tag{29}$$

where: β=by-pass loop parameter; p1 t=the exit age of a particle flowing through the system;

$\bar{t}$=the mean residence time of the particles in the system;

$E(t)_\Gamma$=the outlet concentration for a given unit impulse of a pulsed tracer with a by-pass loop; and Γ=the gamma function=Γ(p)=(p−1)!.

Variable opening volumes for different lung regions, due either to variable stresses in an erect subject or to differing products of resistance and capacitance in the pathways, lead to alveoli opening and filling at different times during the inhalation. Since the regional time constants increase with obstruction, less aerosol can penetrate the obstructed airways to the alveoli. Thus, on exhalation this aerosol emerges unmixed by the action of the alveoli. In addition, the aerosol is also coming from regions with greater time constants that exit more slowly and over a longer period than normal.

The parameter describing the fraction of flow that enters the mixing chamber is defined as letting:

$\beta=Q_1/Q_T$ the fraction of flow entering the mixing section; and $\bar{t}=V/Q_T$ but, $\bar{t}_p=V/Q_1=V/\beta Q_T=\bar{t}/\beta$ where: $\bar{t}$=mean residence time of the entire system;

$\bar{t}_p$=mean residence time of the mixing section;

V=volume of the entire system;

$Q_T$=total flow through the system;

$Q_1$=flow through the mixing section; and $Q_2$=flow by-passing the mixing section.

Therefore, the mixing in the stirred reactors can be described by:

$$E(t)_\Gamma = \frac{(p)^p}{t^p\Gamma(P)}t^{(p-1)}e^{\frac{-pt}{\bar{t}_p}}. \tag{30}$$

However, since $\bar{t}_p=\bar{t}_p/\beta$, Equation (30) can be rewritten as:

$$E(t)_\Gamma = \frac{(p\beta)^p}{\bar{t}^p\Gamma(p)}t^{(p-1)}e^{\frac{-p\beta t}{\bar{t}}}. \tag{31}$$

Equation (30) is the exit-age distribution of the mixing section when there is by-passing. Defining the reduced time as $\theta=t/\bar{t}$, and noting that $E(\theta)_{1'}=\bar{t}\,E(t)_\Gamma$, the exit age distribution of the Γ-mixing section for a unit impulse is given in terms of reduced time θ by:

$$E(\theta)_\Gamma = \frac{(p\beta)^p}{\Gamma(p)}\theta^{(p-1)}e^{-p\beta\theta} \tag{32}$$

Taking the Laplace transform of Equation (31) gives the transfer function for the mixing section alone as:

$$E(s) = \frac{C_1(s)}{C_0(2)} = \left[\frac{p\beta}{s+p\beta}\right]^p. \tag{33}$$

Performing a material balance at the point where the by-pass stream and the mixing section stream join to form the outlet stream we have:

$$C_2Q_t=Q_1C_1+Q_2C_o. \tag{34}$$

Dividing Equation (34) throughout by $Q_t$ and rearranging by substituting for β yields $$C_2Q_t=C_1\beta+(1-\beta)C_o \tag{35}$$

Taking the Laplace transform of Equation (35) and dividing throughout by $C_o(s)$ yields:

$$E(s) = \frac{C_2(s)}{C_0(2)} = \frac{C_2(s)}{C_0(2)}\beta + (1-\beta). \tag{36}$$

Upon substituting Equation (32) in the above equation, the result for the output of the composite is:

$$H(s) = \frac{C_2(s)}{C_0(2)} = \left[\frac{p\beta}{s+p\beta}\right]\beta + (1-\beta). \tag{37}$$

Now, assuming a delta function type input signal for $C_o(s)$, the inverse transform of the function shown in Equation (34) then gives the complete system definition for the output concentration $C_2(\theta)$ in the time domain from the model predicted for an impulse-type input signal, where, δ(θ)=the dirac delta function and $C_2(\theta)$ is given by:

$$C_2(\theta) = \left[\frac{\beta(p\beta)^p}{\Gamma(p)}\right]\theta^{(p-1)}e^{-p\beta\theta} + (1-\beta)\delta(\theta). \tag{38}$$

The first term in Equation (38) describes the mixing of the impulse-type input signal occurring for the amount of air flow entering the mixing chamber accounted for by β. The second term is purely a by-pass term relating to the amount of air by-passing the mixing chamber. The by-passed air is instantly detected at the time when the input impulse is given.

The model parameters p and β can be easily determined from the data collected by the method of moments. However, when the method was used to calculate p and β for an ideal impulse, the method failed to estimate correct values of p and β. Therefore, the present invention performs this parameter estimation function by a curve-fitting technique with the goodness-of-fit measured by minimizing the sum of the differences squared.

The ventilation parameter, p, has a minimum value of 1 for complete (i.e. uniform) mixing. If there is no by-passing ($\beta$=1) and for the special case where p=1, then Equation (37) reduces to the exponential distribution. An increasing value of p is used to model the effect of increased ventilation or reduced homogeneous mixing. As p approaches infinity, no mixing occurs and the output distribution becomes identical to the input distribution. This is the case of perfect ventilation. Increasing values of p also cause the peak-concentration time to occur later, approaching $\theta=1/\beta$ as an upper limit. Since p is actually the number of reactors in series, the result of increasing the number of reaction vessels in series is to decrease the completeness of the mixing for a given volume of the system.

The fraction of flow which enters the mixing section (determined by $\beta$, the by-pass parameter) is used as a measure of the non-homogeneity of ventilation. The underlying assumption is that the fraction of flow which does not enter the ventilation section undergoes no ventilation. That is, based on the assumption that the upper airways contribute relatively little to the ventilation between tidal and residual air, only the fraction of the aerosol which penetrates past the upper airways is assumed to undergo ventilation. As the regional time constants increase, owing to airway obstruction, additional alveoli are recruited along less obstructed pathways. This causes the aerosol in the inhaled bolus to traverse additional airways and more of the air flow stream to by-pass the ventilation section. In other words, a larger fraction of the aerosol remains in the airways rather than penetrating the airspaces. An analogous situation occurs when the depth to which the bolus is inhaled in a healthy subject is decreased. The decreased penetration causes a decrease in the fraction of aerosol penetrating to the airspaces and a decreased value of $\beta$ is observed. A decreasing $\beta$ causes the peak concentration to occur at a later time, where $\theta=1$ as the lower limit. If an increase in mixing occurs, as should be the case for decreased penetration, the peak concentration may be offset, resulting in negligible net movement of the peak.

Therefore, in individuals with airway obstruction or restriction; (1) when the aerosol passes an obstructed airway the value of p or $\beta$ will change; and (2) the volume at which the change in p or $\beta$ occurs is the site of the obstruction and the volume at which the therapeutic aerosol should be injected. In healthy subjects, the values of p and $\beta$ should be seen to fluctuate relatively little at any inhaled volume of aerosol bolus, as long as the aerosol is not inhaled into the gas exchange region of the lung and as long as Equation (37) is solved for the dimensionless volume.

Further, as a non-limiting example of the methods discussed above, the diagnosis of asthma may be done using the content of multiple breaths when a bolus is inhaled on the first breath only. If the bolus of aerosol penetrates beyond the volume at which airways involved in asthma occur, trapping of the aerosol will be seen. This trapping phenomena will be demonstrated by the presence of aerosol in subsequent exhalations after the inhalation of the bolus. Thus, using the method of the present invention, the diagnosis of asthma can be based upon the presence of aerosol in exhalations where no aerosol was introduced on the inhalation portion of that breathing cycle and subsequent to the introduction of aerosol in a prior inhalation. The lowest volume of penetration at which this trapping is seen to initially occur designates the volume at which therapeutic aerosol should be introduced for alleviation of the symptoms of asthma.

Pharmaceutical active agents can also be delivered with the apparatus of the invention. In the preferred embodiment, the active agent is contained in the aerosol generator, and is released with the aerosol. The release of the active agent with the aerosol at the determined point of the breathing cycle helps to ensure that the active agent is delivered to the region of obstruction or inflammation in the lung as determined by the apparatus and method of the invention. Knowledge of the volume of penetration of the aerosol bolus provides the necessary information to deliver the active agent at the obstruction site.

It is to be understood that other embodiments may be utilized and structural changes may be made without departing from the scope of the present invention.

What is claimed is:

1. A method for treating an obstruction in the upper region of the lungs, the method comprising:
    a. measuring pressure data and calculating volume of airflow of a breathing cycle;
    b. providing a volume of penetration;
    c. providing an aerosol bolus at a determined point of the breathing cycle;
    d. measuring a concentration values of aerosol particles and calculating time constants from the measured aerosol concentration values;
    e. repeating steps b to d using a different volume of penetration;
    f. comparing the calculated time constants, in a processing device, from at least two provided volumes of penetration to determine the position of an obstruction; and
    g. releasing a treatment bolus at a select point of the breathing cycle which is chosen based upon the determined position of the obstruction.

2. The method of claim 1, wherein the select point is chosen to concentrate the treatment bolus in a selected volume of air flow determined to contact the position of the obstruction during the breathing cycle.

3. The method of claim 1, wherein the treatment bolus comprises an active pharmaceutical.

4. A method for treating inflammation in the upper region of the lungs, the method comprising:
    a. measuring pressure data and calculating volume of airflow of a breathing cycle;
    b. providing a volume of penetration;
    c. providing an aerosol bolus at a determined point of the breathing cycle;
    d. measuring a concentration values of aerosol particles and calculating time constants from the measured aerosol concentration values;
    e. repeating steps b to d using a different volume of penetration;
    f. comparing the calculated time constants, in a processing device, from at least two provided volumes of penetration to determine the position of inflammation; and
    g. releasing a treatment bolus at a select point of the breathing cycle which is chosen based upon the determined position of the inflammation.

5. The method of claim 4, wherein the select point is chosen to concentrate the treatment bolus in a selected volume of air flow determined to contact the position of the inflammation during the breathing cycle.

6. The method of claim 4, wherein the treatment bolus comprises a bronchial dilating agent.

7. The method of claim 4, wherein the treatment bolus comprises an active pharmaceutical.

* * * * *